(12) United States Patent
Flaishon et al.

(10) Patent No.: US 7,919,077 B2
(45) Date of Patent: Apr. 5, 2011

(54) PHARMACEUTICAL COMPOSITIONS COMPRISING CCL2 AND USE OF SAME FOR THE TREATMENT OF INFLAMMATION

(75) Inventors: Liat Flaishon, Ramat-Gan (IL); Idit Shachar, Ramat-Gan (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

(21) Appl. No.: 12/309,611

(22) PCT Filed: Jun. 28, 2007

(86) PCT No.: PCT/IL2007/000806
§ 371 (c)(1),
(2), (4) Date: Jan. 23, 2009

(87) PCT Pub. No.: WO2008/012796
PCT Pub. Date: Jan. 31, 2008

(65) Prior Publication Data
US 2009/0239799 A1    Sep. 24, 2009

Related U.S. Application Data

(60) Provisional application No. 60/832,600, filed on Jul. 24, 2006.

(51) Int. Cl.
*A61K 38/19* (2006.01)
*C07K 14/52* (2006.01)
(52) U.S. Cl. .......................... 424/85.1; 514/12; 530/350
(58) Field of Classification Search ........................ None
See application file for complete search history.

(56) References Cited

U.S. PATENT DOCUMENTS

2007/0092484 A1 * 4/2007 Levine et al. ................ 424/85.1

OTHER PUBLICATIONS

Rose et al, Microcirculation, 2003, vol. 10, pp. 273-288.*
Nankano et al, Infection and Immunity, 1994, vol. 62 No. 2, pp. 377-383.*
International Search Report and the Written Opinion Dated Mar. 27, 2008 From the International Searching Authority Re.: Application No. PCT/IL07/00806.

* cited by examiner

*Primary Examiner* — Bridget E Bunner
*Assistant Examiner* — Fozia M Hamud

(57) ABSTRACT

A method of treating an inflammation in a subject thereof is provided. The method comprising administering to the subject a therapeutically effective amount of CCL2, thereby treating the inflammation. Also provided are pharmaceutical compositions and unit dosage forms which comprise CCL2 for the treatment of inflammation.

5 Claims, 10 Drawing Sheets

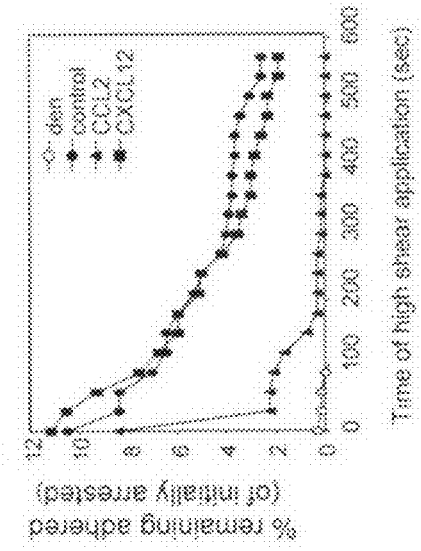
Fig. 6a
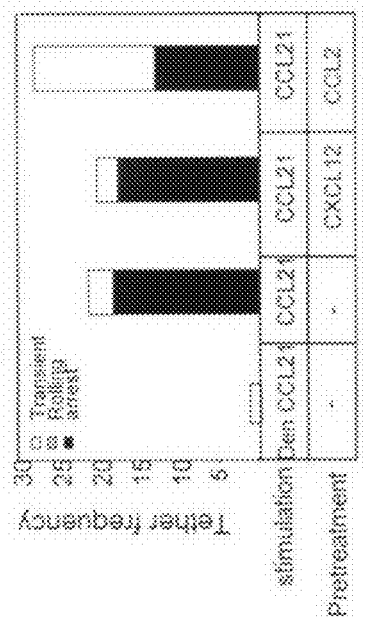
Fig. 6b
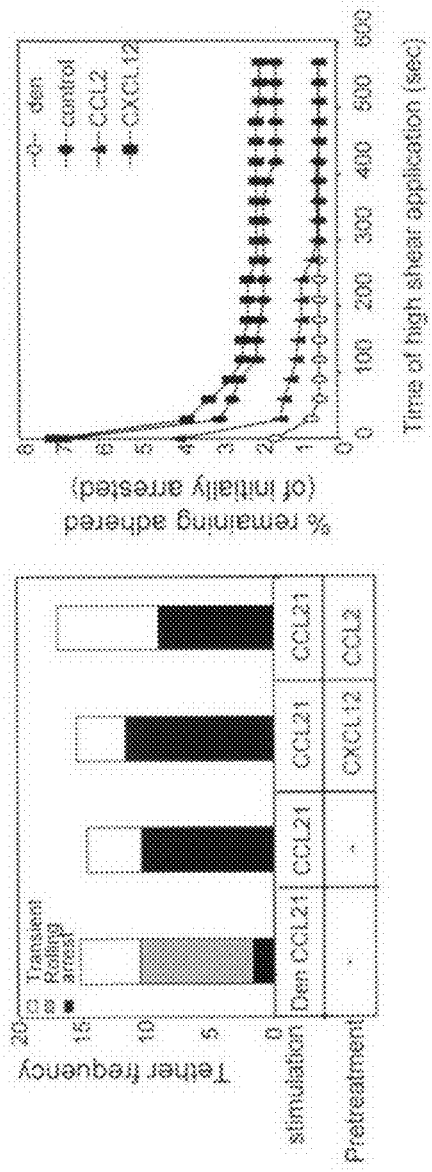
Fig. 6c
Fig. 6d

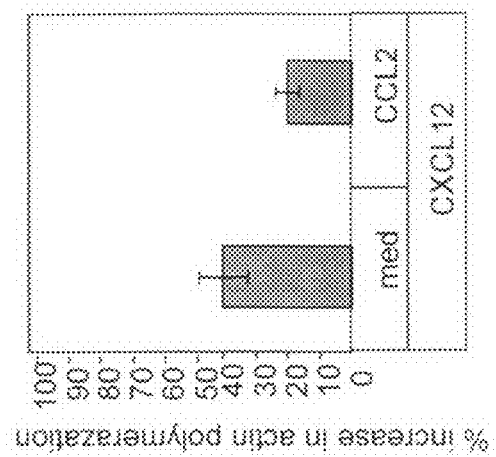
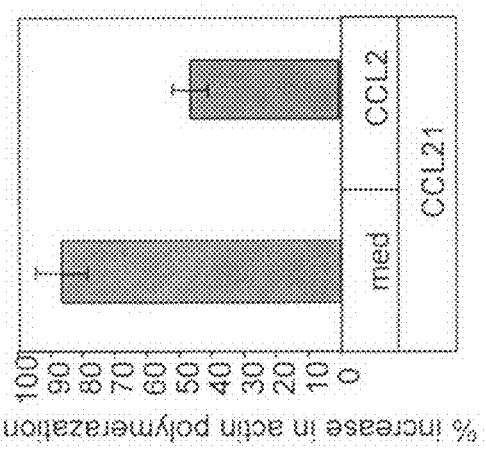
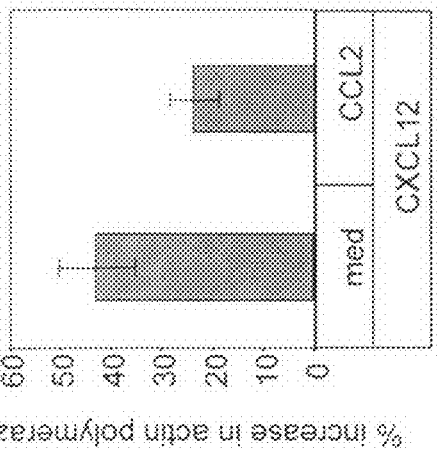
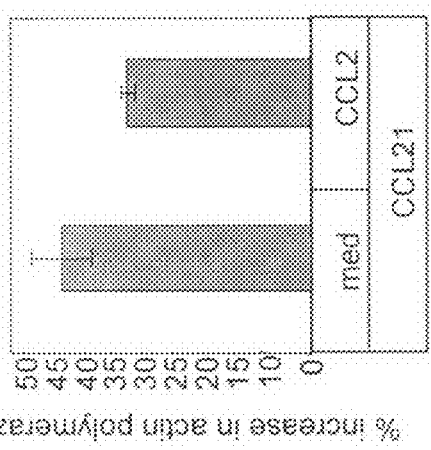
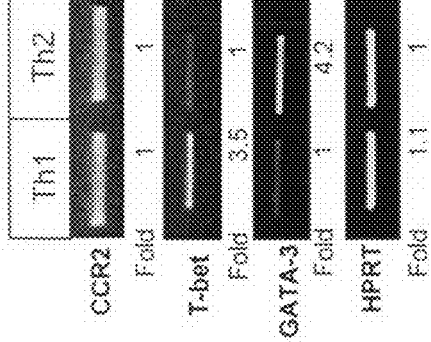

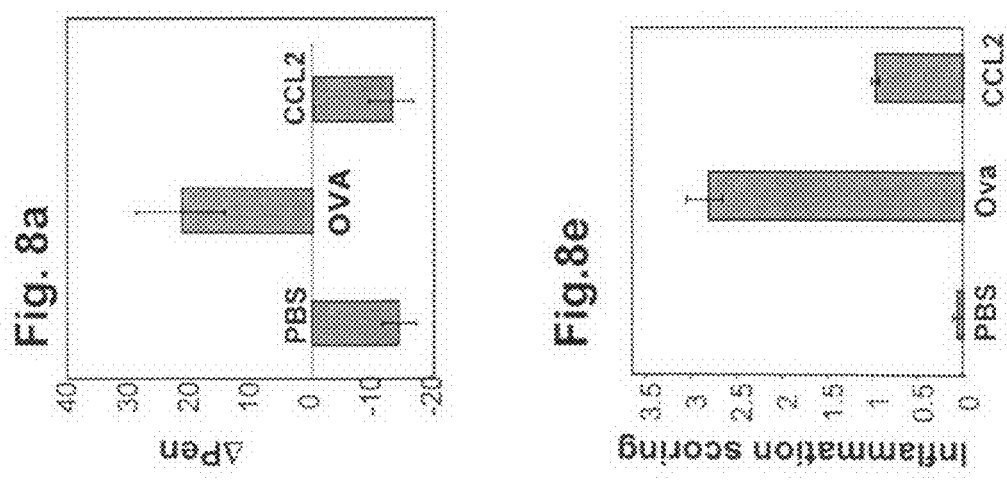

SEQUENCE LISTING

```
<160> NUMBER OF SEQ ID NOS: 9

<210> SEQ ID NO 1
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 1
atgttacctc agttcatcca c                                              21

<210> SEQ ID NO 2
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 2
gcccacaaaa ccaaagatga at                                             22

<210> SEQ ID NO 3
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 3
gagggtaggc tggcctatgg ct                                             22

<210> SEQ ID NO 4
<211> LENGTH: 25
<212> TYPE: DNA
<213> ORGANISM: Artificial sequence
```

```
<220> FEATURE:
<223> OTHER INFORMATION: Single strand DNA oligonucleotide

<400> SEQUENCE: 4
gttggataca ggccagactt tgttg                                             25

<210> SEQ ID NO 5
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 5
ttcccattcc tgtccttcac cg                                                22

<210> SEQ ID NO 6
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 6
ggaaggtcgg ggtaaaaac                                                    19

<210> SEQ ID NO 7
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 7
tctggaggaa acgctaatgg                                                   20

<210> SEQ ID NO 8
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 8
gaactcttcg cacacttgga gactc                                             25

<210> SEQ ID NO 9
<211> LENGTH: 99
<212> TYPE: PRT
<213> ORGANISM: Homo sapiens

<400> SEQUENCE: 9
```

Met Lys Val Ser Ala Ala Leu Leu Cys Leu Leu Leu Ile Ala Ala Thr
1               5                   10                  15

Phe Ile Pro Gln Gly Leu Ala Gln Pro Asp Ala Ile Asn Ala Pro Val
            20                  25                  30

Thr Cys Cys Tyr Asn Phe Thr Asn Arg Lys Ile Ser Val Gln Arg Leu
        35                  40                  45

Ala Ser Tyr Arg Arg Ile Thr Ser Ser Lys Cys Pro Lys Glu Ala Val
    50                  55                  60

-continued

```
Ile Phe Lys Thr Ile Val Ala Lys Glu Ile Cys Ala Asp Pro Lys Gln
65                  70                  75                  80

Lys Trp Val Gln Asp Ser Met Asp His Leu Asp Lys Gln Thr Gln Thr
                85                  90                  95

Pro Lys Thr
```

US 7,919,077 B2

PHARMACEUTICAL COMPOSITIONS COMPRISING CCL2 AND USE OF SAME FOR THE TREATMENT OF INFLAMMATION

RELATED APPLICATIONS

This Application is a National Phase of PCT Patent Application No. PCT/IL2007/000806 having International filing date of Jun. 28, 2007, which claims the benefit of U.S. Provisional Patent Application No. 60/832,600 filed on Jul. 24, 2006. The contents of the above Applications are all incorporated herein by reference.

FIELD AND BACKGROUND OF THE INVENTION

The present invention relates to pharmaceutical compositions which comprise CCL2 and methods of using same for the treatment of inflammation such as associated with allergy and autoimmune diseases.

While the invention will be described herein in more detail with respect to the treatment of inflammation associated with asthma and autoimmune diseases, it is to be understood that the invention is applicable to the treatment of any medical condition associated with CCR2/CCL2 dependent cell migration.

The surveillance of the body for foreign antigens is a critical function of the immune system. An important part of antigen recognition, is the unceasing migration of B and T cells in and out of lymph nodes from the bloodstream across the specialized endothelial walls of blood vessels, located in specific areas of lymphoid organs, called high endothelial venules (HEV). This migration increases the probability of encounter between antigen and the appropriate B and T cell, an encounter essential for recognition and initiation of an immune response. For a review of homing and cellular migration in lymph nodes see von Adrian and Mempel [Nature reviews, Immunology, 3: 867-876 (2003)].

T-cells play a key role in initiating and perpetuating inflammation, via the production of soluble mediators in addition to cell/cell contact interactions with a variety of cell types through membrane receptors and their ligands. T-cell subsets express unique patterns of homing molecules to interact with organ-specific cells for preferential recruitment to distinct target tissues. Indeed, chemo-attractants and cellular activators are among others, responsible for neutrophil trafficking into inflamed tissues, as well as for lymphocyte homing into foci of chronic inflammation.

A specific malfunction of the immune system occurs when lymphocytes and eosinophils infiltrate the airway wall of the lung and eventually cause asthma. This chronic inflammatory disorder of the bronchial airways is characterized by intermittent episodes of airway obstruction and wheezing. Specific symptoms include variable airflow obstruction, airway hyper-responsiveness (AHR) and airway inflammation. Although asthma is multifactorial in origin, it has been suggested that T lymphocytes, and in particular $CD4^+$ T cells producing a Th2 pattern of cytokines, have a prominent effect on the pathogenesis of this disease while T helper 1 cells regulate allergic airway inflammation and mucus production. [Cohn, L., et al., J. Exp. Med. 190:1309 (1999)].

Current treatments for asthma include relieving bronchodilators based on β2 adrenergic receptor agonists, which cause immediate relief of the symptoms, but do not treat the disease; and long term therapy based on anti-inflammatory treatments. Treatment of asthma, however, remains unsatisfactory in that in most cases it is life long, requiring larger or more frequent doses of medicine. This results in either abandoned or misused treatment by the subject, due to its inconvenience, or to increased side effects associated with prolonged use of the medicine, often compromising patient's life quality, as well as increasing the risk of drug resistance. Long term use of beta agonists also involves pronounced side effects, including tachycardia (rapid heartbeat), skeletal muscle tremor, hypokalemia, increased lactic acid, headache, and hyperglycemia.

Another malfunction of the immune system occurs when immune cells attack the bodies own cells and tissues resulting in an autoimmune disease, such as rheumatoid arthritis (RA) and inflammatory bowel disease (IBD, e.g. colitis). Rheumatoid arthritis is a chronic inflammatory autoimmune disease of the joints. Although the cause of RA is currently unknown, once triggered, the immune response including CD4+ and CD8+ T cells, cause inflammation of the synovium. RA is also a systemic disease affecting extra-articular tissues throughout the body including the skin, blood vessels, heart, lungs and muscles. Currently there is no known cure for rheumatoid arthritis and the main goal of treatment is to reduce joint inflammation and pain, maximize joint function and prevent joint destruction and deformity.

IBD, mainly Crohn's disease and ulcerative colitis (UC), are autoimmune inflammatory conditions affecting the gastrointestinal tract. IBD is currently believed to be caused by activation of mucosal T lymphocytes and in particular CD4+ T cells [Neurath, AGAH 2003, 2:op019]. Current treatments of IBD include anti-inflammatory drugs and immunosuppressive drugs (including steroid based, further explained hereinbelow). However, these treatments remain unsatisfactory and IBD remains a life long disease requiring larger and sometimes frequent doses of medicine.

Anti-inflammatory drugs, for treatment of asthma in particular and autoimmune diseases in general, include steroid based medicines, taken either by inhalation or orally, both accompanied by side effects. These include hoarseness of the voice and a sore throat (usually together with fungal infection) in inhaled dosages, and more severe risks involved with long term use or oral administration, including loss of adrenal function and growth hormone production (leading among others, to growth retardation in children), increased susceptibility to infection, slow healing, salt retention (leading to leg swelling, raised blood pressure, weight increase and heart failure), tremor, increased susceptibility to eye disease, particularly glaucoma and cataract, skin thinning resulting in easy bruising (purpura), thinning of the bones (osteoporosis) and more.

Anti-inflammatory treatment with leukotriene modifiers was thought to be advantageous in that it does not involve pronounced side effects, but the efficiency of these drugs is controversial. Leukotriene modifiers block a specific part of the inflammatory cascade that typically occurs in asthma and autoimmune conditions, and is thought to be limited only to specific subsets of patients. Furthermore, like other treatments, these need to be taken as a prophylactic, and insufficient or inefficient self administration further reduces their efficiency.

Other asthma therapies are based on mast cell inhibitors like cromolyn sodium and nedocromil sodium which prevent the release of histamines. However, these drugs are not potent, do not relieve severe symptoms or symptoms which have already started, are required to be taken four times a day and start taking effect only after a period of a month.

Asthma, rheumatoid arthritis and IBD therefore remain chronic diseases which require life long treatment, accompanied with inconvenient use of drugs together with unwanted side effects.

Previous studies on inflammatory conditions, including asthma, focused on the recruitment of leukocytes to the lymph nodes (LN) or sites of inflammation. However, little is known about the molecular mechanisms that negatively control or prevent homing of cells to these sites, thereby contributing to the fine tuning of the immune response at specific lymphoid and peripheral tissues.

Recently two pathways that negatively regulate homing of B cells to the lymph nodes were characterized. It was found that immature B cells can down regulate their own integrin-mediated adhesion to the extracellular matrix and thereby suppress their migration into non-splenic sites [Flaishon, L. et al., J. Exp. Med. 192:1381(2000)]. This inhibition is mediated by two independent pathways. The first one involves the secretion of IFN-γ by immature B cells, which interacts with its receptor, and causes inhibition of cytoskeleton rearrangement, required for promoting integrin-mediated adhesion and migration of B cells. The second pathway is regulated by the chemokine receptor, CCR2. In an analysis done with mice lacking CCR2, it was found that CCR2 downregulates immature B cell homing to the lymph nodes independently of the negative regulation of IFN-γ. This was determined by the elevation of immature CCR2−/− B cells migration and cytoskeletal rearrangement as a response to SDF-1 stimulation, and by the elevation of CCR2−/− B-cell homing to the LN. CCR2 is normally expressed on murine immature B cells and its expression is downregulated following differentiation to the mature stage [Flaishon, L., et al., Blood 104:933. (2004)].

CCL2, (also called Macrophage Chemotactic Protein-1 or MCP-1) is particularly highly expressed during inflammation, and is a potent monocyte as well as a lymphocyte chemoattractant. CCL2 activates CCR2 on rolling monocytes, triggering integrin mediated arrest. CCL2 is also one of the strongest histamine inducing factors.

Most studies and medical applications of the CCL2/CCR2 interaction suggest downregulating CCL2/CCR2 functions as a possible modality for the treatment of cancer [e.g. ovarian cancer: Sica, A. et al., J. Immunology (2000) 164(2):733-8)], inflammatory diseases [e.g., human crescentic glomerulonephritis: Segerer et al. J. Am. Soc. Nephrol. 11:2231-2242 (2000)] and autoimmune reactions [e.g., the significant role CCL2 appears to play during the early stages of allergic responses because of its ability to induce mast cell activation, directly inducing AHR (airways hyper-responsiveness; Campbell et al., J Immunol 163:2160-2167 (1999)].

U.S. patent applications 20050232923, 20050058639, 20050054668, 20040138171, 20040047860, 20020106355 and 20020099054 are just a few of many examples of suggested teachings for treating various diseases by antagonizing the CCL2/CCR2 interaction. The potential therapeutic value of antagonism of the CCL2/CCR2 interaction was utilized for example in treating asthma. Sequestration of CCL2 with a neutralizing antibody in ovalbumin-challenged mice resulted in marked decrease in bronchial hyper-responsiveness and inflammation [Jose-Angel Gonzalo, et al., J. Exp. Med. 1998, 188, 157]. In another study, MCP-1−/− mice displayed a reduced response to challenge with Schistosoma mansoni egg [Bao Lu, et al., J. Exp. Med. 1998, 187, 601].

Thus, to date, treatment of inflammatory diseases by administration of CCL2 has never been suggested.

There is thus a widely recognized need for pharmaceutical compositions which comprise CCL2 and methods of using same for treating inflammation, devoid of the above limitations.

SUMMARY OF THE INVENTION

According to one aspect of the present invention there is provided a method of treating an inflammation in a subject in need thereof, the method comprising administering to the subject a therapeutically effective amount of CCL2, thereby treating the inflammation.

According to further features in preferred embodiments of the invention described below, the subject is a human subject.

According to still further features in the described preferred embodiments, the therapeutically effective amount is 1 ng-1 µg per kilogram body weight/day.

According to still further features in the described preferred embodiments, the therapeutically effective amount is selected so as to avoid unwanted side-effects associated with elevated concentrations of CCL2.

According to still further features in the described preferred embodiments, the therapeutically effective amount is selected to inhibit cell migration or homing.

According to still further features in the described preferred embodiments, the cell is a CCR2 expressing cell.

According to still further features in the described preferred embodiments, the cell is an immune cell or a cancer cell.

According to still further features in the described preferred embodiments, the inflammation is associated with CCR2/CCL2 dependent cell migration or homing.

According to still further features in the described preferred embodiments, the cell migration or homing comprises T-cell migration or homing.

According to still further features in the described preferred embodiments, the inflammation is associated with allergy.

According to still further features in the described preferred embodiments, the allergy is asthma.

According to still further features in the described preferred embodiments, the inflammation is associated with an autoimmune disease.

According to still further features in the described preferred embodiments, the autoimmune disease is Rheumatoid Arthritis.

According to still further features in the described preferred embodiments, the autoimmune disease is Inflammatory Bowel Disease.

According to still further features in the described preferred embodiments, the inflammation is associated with a medical condition selected from the group consisting of cancer, autoimmune, hypersensitivity, diabetes, infectious, transplantation associated and allergy.

According to another aspect of the present invention there is provided a pharmaceutical composition comprising, as an active ingredient, CCL2 and a pharmaceutically acceptable carrier.

According to yet another aspect of the present invention there is provided the use of CCL2 for the manufacture of a medicament identified for treating an inflammation.

According to still another aspect of the present invention there is provided a unit dosage form comprising CCL2.

According to still further features in preferred embodiments of the invention described below, the unit dosage form comprises 1 ng-200 µg.

According to still further features in the described preferred embodiments, the unit dosage form is an oral unit dosage form.

According to still further features in the described preferred embodiments, the unit dosage form is an injectable unit dosage form or an inhaled unit dosage form.

According to still another aspect of the present invention there is provided a method of regulating cell migration, the method comprising contacting the cell with a medium comprising an amount of CCL2 selected to inhibit cell migration, thereby regulating cell migration.

According to still further features in preferred embodiments of the invention described below, the cell is a CCR2 expressing cell.

According to still further features in the described preferred embodiments, the cell is an immune cell or a cancer cell.

According to still further features in the described preferred embodiments, the medium further comprises a cell-migration promoting agent.

The present invention successfully addresses the shortcomings of the presently known configurations by providing pharmaceutical compositions which comprise CCL2 and methods of using same for treating inflammation, such as associated with allergy.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1a depicts the expression of CCR2 or control gene (HPRT) produced from purified CD4+ and CD8+ T cells, as indicated. FIG. 1b depicts the expression of CCR2 produced from naïve CD4+ cells and Th1 or Th2 populations that were skewed there from. The results presented represent three different experiments. Note the higher expression of CCR2 in CD4+ T cell population as compared to naïve T cells or Th1 and Th2 skewed CD4+ T cell populations.

FIGS. 2a and 2b depict the results of a Transwell migration assay. Naïve T cells pre-treated with medium or CCL2, were placed in the upper well of a Transwell plate in the presence of CXCL12 (FIG. 2a) or SLC (CCL21, FIG. 2b). Following 3 hours, the number of the migrating cells found in the lower chamber was evaluated by FACS analysis. Results from 3 different experiments are presented in migration percentage, being the number of migrating cells in the lower chamber as a fraction of the input cells in the upper chamber; FIGS. 2c-e depict CCL2 influence on cytoskeleton rearrangement. Naïve T cells were stimulated with CXCL12 (FIG. 2c) or SLC (CCL21, FIG. 2d) in the presence or absence of CCL2 (0.1 ng/ml). Naïve T cells were stimulated with CCL21 (0.4 mg/ml) in the presence or absence of Rantes, Mip1β, Eotoxin or CXCL12 (0.1 ng/ml, FIG. 2e). Thereafter, the cells were fixed and permeabilized, and their intracellular F-actin was stained with FITC-phalloidin. The change in polymerized actin was analyzed by FACS. Results from three different experiments are presented as the increase of actin polymerization (percentage) resulting from chemokine stimulation.

FIG. 5a shows intravital micrograph and its sketch of a typical subiliac LN at low (×5) magnification. LN venous blood drains into an extralymphoid side branch of the superficial epigastric vein via the LOVs (orders I, II and some of order III venules) and the HEVs (orders III, IV and V venules); FIG. 5b shows rolling fractions and FIGS. 5c-e shows sticking fractions of calcein-labeled naive control or CCL2-treated lymphocytes in the venular tree of subiliac LNs. Lymphocytes were pre-treated with CCL2 (1 ng/ml for 30 minutes) or left untreated and injected into the femoral artery. Rolling fraction is calculated by 100× nbr of rolling cells/nbr fast cells. Sticking fraction is calculated by 100× nbr of arrested cells (more than 10 seconds or 30 seconds or 1 minute)/nbr of rolling cells. Data shown are means±SEM of 3-5 venules per mouse (n=3 animals analyzed); FIGS. 5f-g show intravital micrograph (10×) of lymphocyte arrest in the PLN venular tree. The accumulation of CCL2-treated (FIG. 5f) or control (FIG. 5g) lymphocytes in PLN venules was analyzed 30 minutes after intravenous injection of the fluorescently labeled cells.

FIGS. 6a-d are graphs depicting how low dose CCL2 does not interfere with rapid LFA-1 or VLA-4 activation by CCL21 but impairs post arrest adhesion strengthening. FIGS. 6a and 6c show frequency and strength of adhesive tethers between human T cells (intact or CCL2 pre treated) interacting with ICAM-1 (FIG. 6a) or VCAM-1 (FIG. 6c), each coated alone or co-immobilized with heat inactive or functional CCL21 at a shear stress of 0.5 dyn/cm² and 0.75 dyn/cm², respectively. FIG. 6b and 6d show human T cells (intact or CCL2 pre treated) which were allowed to accumulate for 2 minutes and their adhesion persistence (ability to resist detachment) by a constant application of high shear stress (5 dyn/cm$^2$) for the indicated time points was assessed. Results of ICAM-1 (FIG. 6b) or VCAM-1 (FIG. 6d) are shown as % of cells initially accumulated at low shear flow.

FIGS. 7a-e are graphs depicting CCR2 expression on effector T cells and CCL2 inhibition of effector T cell migration in vitro. FIG. 7a shows Th1 and Th2 cell populations. RNA was isolated and levels of CCL2, T-bet, GATA-3 or HPRT mRNA were analyzed; FIGS. 7b-c show effector (Th1) cells stimulated with CCL21 (0.4 mg/ml, FIG. 7b) or CXCL12 (0.1 ng/ml, FIG. 7c) for 15 seconds in the presence or absence of CCL2 (0.1 ng/ml), fixed, permeabilized, and their intracellular F-actin was stained with FITC-phalloidin. The change in polymerized actin was analyzed by FACS. Percent increase in actin polymerization was calculated as the polymerization of actin in the presence of chemokine stimulation [minus] polymerization of actin without chemokine/polymerization of actin without chemokine. FIGS. 7d-e show effector (Th2) cells stimulated with CXCL12 (0.1 mg/ml, FIG. 7d) or CCL21 (0.4 mg/ml, FIG. 7e) for 15 seconds in the presence or absence of CCL2 (0.1 ng/ml), fixed and permeabilized, and their intracellular F-actin was stained with FITC-phalloidin. The change in polymerized actin was analyzed by FACS. Percent increase in actin polymerization was calculated as the polymerization of actin in the presence of chemokine stimulation [minus] polymerization of actin without chemokine/polymerization of actin without chemokine. The results presented are representatives of 3 different experiments.

FIGS. 8a-e are graphs depicting the inhibition of an allergic response by CCL2 in a mouse asthma model. FIG. 8a shows control (PBS treated), OVA-primed mice (OVA) and OVA-primed mice injected i.p. with CCL2 (60 ng) analyzed for airway responsiveness on day 15. Values shown represent AΔ Penn, which was calculated by subtracting control Penn measurements before antigen challenge from the Penn measurements after late or early antigen challenge. Baseline Penn levels were comparable among PBS treated control, ova-primed mice, and ova-primed mice, treated with CCL2. The results represent an average of 9 animals per treatment; FIGS. 8b-d show lung histology of CCL2 treated mice. Histological features of control (PBS, FIG. 8b), ova-primed (OVA, FIG. 8c) and ova-primed treated with CCL2 (CCL2, FIG. 8d). Note a pleomorphic peribronchial and perivascular infiltrate consisting mainly of eosinophils and lymphocytes seen only in lung tissue from OVA primed mice (FIG. 8c) and not in PBS-challenged or CCL2-treated mice; FIG. 8e shows the peribronchial and perivascular inflammatory infiltrates given an inflammatory score of between 1-4 by a pathologist in control (PBS treated) OVA primed (OVA) and OVA primed and CCL2 injected (CCL2) mice. The graph represents the scores of 9 animals.

DESCRIPTION OF THE PREFERRED EMBODIMENTS

Figure 1B:
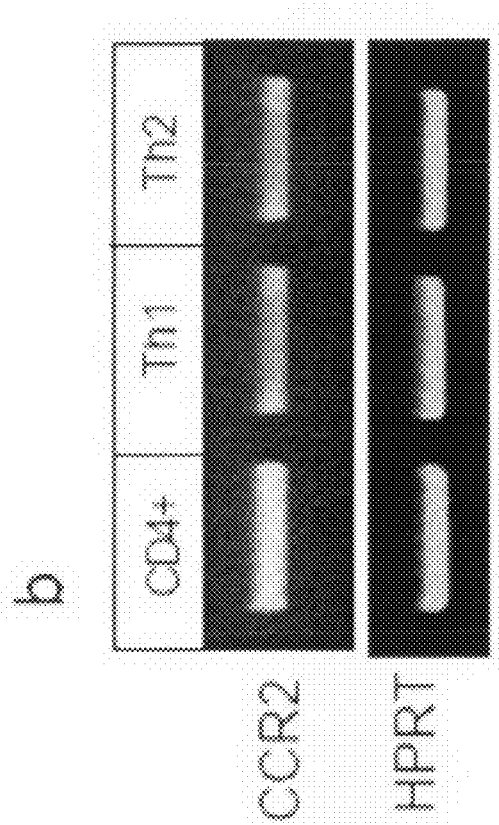
FIGS. 1a-b are PCR images showing expression of CCR2 in naïve and effector T cells.

The present invention is of pharmaceutical compositions which comprise CCL2 and methods of using same for the treatment of inflammation such as associated with allergy.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

CCL2 also termed, Monocyte chemoattractant protein (MCP-1), is well known to specifically attract monocytes and memory T cells. Its expression occurs in a variety of diseases characterized by cell migration, and there is substantial biological and genetic evidence for its essential role in inflammatory diseases. Numerous studies suggest antagonizing CCL2/CCR2 for the treatment of inflammatory diseases (e.g., allergy and cancer, see Background section).

However, to date it has never been suggested to use CCL2 for the treatment of inflammation.

Whilst reducing the present invention to practice, the present inventors have surprisingly uncovered that administration of low doses of CCL2 (rather than its inhibition) may be used to effectively reduce T-cell migration and as such may be used for the treatment of inflammation.

As is shown hereinbelow and in the Examples section which follows the present inventors have shown that low levels of CCL2 specifically down-regulate cytoskeleton rearrangement and migration of naïve and effector T cells in vitro (Examples 1 and 5) and inhibit T cells homing into lymph nodes in-vivo (Example 2). Furthermore, CCL2 treatment renders T cells defective in CCL21-triggered VLA-4-dependent adhesion strengthening to VCAM-1 (Example 3). Notably, CCL2 pretreatment did not affect rolling and earliest events of integrin-mediated arrest but rather influenced a later stage inhibiting integrin-dependent lymphocyte firm adhesion to and extravasation across HEV walls in the mouse peripheral lymph nodes (Example 3). The results have further shown that pretreatment with CCL2 resulted in failure of T cells to develop adhesion strengthening and thus they readily detached from their integrin ligands when continuously exposed to high shear stress (Example 4). In vivo models have shown that CCL2 has a dramatic anti-inflammatory effect in asthma, rheumatoid arthritis and inflammatory bowel disease (colitis, Example 6).

These results support, for the first time, the use of CCL2 polypeptide for the treatment of inflammation.

Thus, according to one aspect of the present invention there is provided a method of treating an inflammation in a subject in need thereof. The method comprising administering to the subject a therapeutically effective amount of CCL2 polypeptide, thereby treating the inflammation.

As used herein the term "subject in need thereof" refers to a mammal, preferably a human subject which may benefit from the treatment modality of the present invention. Preferably the subject does not suffer from a medical condition which is not associated with inflammation.

As used herein the term "treating" refers to preventing, curing, reversing, attenuating, alleviating, minimizing, suppressing or halting the deleterious effects of inflammation.

As used herein the term "inflammation" refers to any medical condition which comprises an inflammatory response in which migration of cells which express CCR2 contributes to inflammation onset or progression. Preferably inflammation is associated with allergy, asthma, IBD (e.g., colitis) or rheumatoid arthritis.

A number of diseases and conditions, which involve an inflammatory response, can be treated using the methodology described hereinabove. Examples of such diseases and conditions are summarized infra.

Inflammatory diseases—Include, but are not limited to, chronic inflammatory diseases and acute inflammatory diseases.

Inflammatory Diseases Associated with Hypersensitivity

Examples of hypersensitivity include, but are not limited to, Type I hypersensitivity, Type II hypersensitivity, Type III hypersensitivity, Type IV hypersensitivity, immediate hypersensitivity, antibody mediated hypersensitivity, immune complex mediated hypersensitivity, T lymphocyte mediated hypersensitivity and DTH.

Type I or immediate hypersensitivity, such as asthma.

Type II hypersensitivity include, but are not limited to, rheumatoid diseases, rheumatoid autoimmune diseases, rheumatoid arthritis (Krenn V. et al., Histol Histopathol 2000 July; 15 (3):791), spondylitis, ankylosing spondylitis (Jan Voswinkel et al., Arthritis Res 2001; 3 (3): 189), systemic diseases, systemic autoimmune diseases; systemic lupus erythematosus (Erikson J. et al., Immunol Res 1998; 17 (1-2): 49), sclerosis, systemic sclerosis (Renaudineau Y. et al., Clin Diagn Lab Immunol. 1999 March; 6 (2):156); Chan O T. et al., Immunol Rev 1999 June; 169:107), glandular diseases, glandular autoimmune diseases, pancreatic autoimmune diseases, diabetes, Type I diabetes (Zimmet P. Diabetes Res Clin Pract 1996 October; 34 Suppl:S125), thyroid diseases, autoimmune thyroid diseases, Graves' disease (Orgiazzi J. Endocrinol Metab Clin North Am 2000 June; 29 (2):339), thyroiditis, spontaneous autoimmune thyroiditis (Braley-Mullen H. and Yu S, J Immunol 2000 December 15; 165 (12):7262), Hashimoto's thyroiditis (Toyoda N. et al., Nippon Rinsho 1999 August; 57 (8):1810), myxedema, idiopathic myxedema (Mitsuma T. Nippon Rinsho. 1999 August; 57 (8): 1759); autoimmune reproductive diseases, ovarian diseases, ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), repeated fetal loss (Tincani A. et al., Lupus 1998;7 Suppl 2:S107-9), neurodegenerative diseases, neurological diseases, neurological autoimmune diseases, multiple sclerosis (Cross A H. et al., J Neuroimmunol 2001 Jan. 1; 112 (1-2): 1), Alzheimer's disease (Oron L. et al., J Neural Transm Suppl. 1997; 49:77), myasthenia gravis (Infante A J. And Kraig E, Int Rev Immunol 1999; 18 (1-2):83), motor neuropathies (Komberg A J. J Clin Neurosci. 2000 May; 7 (3):191), Guillain-Barre syndrome, neuropathies and autoimmune neuropathies (Kusunoki S. Am J Med Sci. 2000 April; 319 (4):234), myasthenic diseases, Lambert-Eaton myasthenic syndrome (Takamori M. Am J Med Sci. 2000 April; 319 (4):204), paraneoplastic neurological diseases, cerebellar atrophy, paraneoplastic cerebellar atrophy, non-paraneoplastic stiff man syndrome, cerebellar atrophies, progressive cerebellar atrophies, encephalitis, Rasmussen's encephalitis, amyotrophic lateral sclerosis, Sydeham chorea, Gilles de la Tourette syndrome, polyendocrinopathies, autoimmune polyendocrinopathies (Antoine J C. and Honnorat J. Rev Neurol (Paris) 2000 January; 156 (1):23); neuropathies, dysimmune neuropathies (Nobile-Orazio E. et al., Electroencephalogr Clin Neurophysiol Suppl 1999; 50:419); neuromyotonia, acquired neuromyotonia, arthrogryposis multiplex congenita (Vincent A. et al., Ann N Y Acad Sci. 1998 May 13; 841:482), cardiovascular diseases, cardiovascular autoimmune diseases, atherosclerosis (Matsuura E. et al., Lupus. 1998; 7 Suppl 2:S135), myocardial infarction (Vaarala 0. Lupus. 1998; 7 Suppl 2:S132), thrombosis (Tincani A. et al., Lupus 1998; 7 Suppl 2:S107-9), granulomatosis, Wegener's granulomatosis, arteritis, Takayasu's arteritis and Kawasaki syndrome (Praprotnik S. et al., Wien Klin Wochenschr 2000 Aug. 25; 112 (15-16):660); anti-factor VIII autoimmune disease (Lacroix-Desmazes S. et al., Semin Thromb Hemost.2000; 26 (2):157); vasculitises, necrotizing small vessel vasculitises, microscopic polyangiitis, Churg and Strauss syndrome, glomerulonephritis, pauci-immune focal necrotizing glomerulonephritis, crescentic glomerulonephritis (Noel L H. Ann Med Inteme (Paris). 2000 May; 151 (3):178); antiphospholipid syndrome (Flamholz R. et al., J Clin Apheresis 1999; 14 (4):171); heart failure, agonist-like beta-adrenoceptor antibodies in heart failure (Wallukat G. et al., Am J Cardiol. 1999 Jun. 17; 83 (12A):75H), thrombocytopenic purpura (Moccia F. Ann Ital Med Int. 1999 April-June; 14 (2):114); hemolytic anemia, autoimmune hemolytic anemia (Efremov D G. et al., Leuk Lymphoma 1998 January; 28 (3-4):285), gastrointestinal diseases, autoimmune diseases of the gastrointestinal tract, intestinal diseases, chronic inflammatory intestinal disease (Garcia Herola A. et al., Gastroenterol Hepatol. 2000 January; 23 (1):16), celiac disease (Landau Y E. and Shoenfeld Y. Harefuah 2000 Jan. 16; 138 (2):122), autoimmune diseases of the musculature, myositis, autoimmune myositis, Sjogren's syndrome (Feist E. et al., Int Arch Allergy Immunol 2000 September; 123 (1):92); smooth muscle autoimmune disease (Zauli D. et al., Biomed Pharmacother 1999 June; 53 (5-6):234), hepatic diseases, hepatic autoimmune diseases, autoimmune hepatitis (Manns M P. J Hepatol 2000 August; 33 (2):326) and primary biliary cirrhosis (Strassburg C P. et al., Eur J Gastroenterol Hepatol. 1999 June; 11 (6):595).

Type IV or T cell mediated hypersensitivity, include, but are not limited to, rheumatoid diseases, rheumatoid arthritis (Tisch R, McDevitt H O. Proc Natl Acad Sci U S A 1994 Jan. 18; 91 (2):437), systemic diseases, systemic autoimmune diseases, systemic lupus erythematosus (Datta S K., Lupus 1998; 7 (9):591), glandular diseases, glandular autoimmune diseases, pancreatic diseases, pancreatic autoimmune diseases, Type 1 diabetes (Castano L. and Eisenbarth G S. Ann. Rev. Immunol. 8:647); thyroid diseases, autoimmune thyroid diseases, Graves' disease (Sakata S. et al., Mol Cell Endocrinol 1993 March; 92 (1):77); ovarian diseases (Garza K M. et al., J Reprod Immunol 1998 February; 37 (2):87), prostatitis, autoimmune prostatitis (Alexander R B. et al., Urology 1997 Dec; 50 (6):893), polyglandular syndrome, autoimmune polyglandular syndrome, Type I autoimmune polyglandular syndrome (Hara T. et al., Blood. 1991 Mar. 1; 77 (5): 1127), neurological diseases, autoimmune neurological diseases, multiple sclerosis, neuritis, optic neuritis (Soderstrom M. et al., J Neurol Neurosurg Psychiatry 1994 May; 57 (5):544), myasthenia gravis (Oshima M. et al., Eur J Immunol 1990 Dec; 20 (12):2563), stiff-man syndrome (Hiemstra H S. et al., Proc Natl Acad Sci U S A 2001 March 27; 98 (7):3988), cardiovascular diseases, cardiac autoimmunity in Chagas' disease (Cunha-Neto E. et al., J Clin Invest 1996 Oct. 15; 98 (8):1709), autoimmune thrombocytopenic purpura (Semple J W. et al., Blood 1996 May 15; 87 (10):4245), anti-helper T lymphocyte autoimmunity (Caporossi A P. et al., Viral Immunol 1998; 11 (1):9), hemolytic anemia (Sallah S. et al., Ann Hematol 1997 March; 74 (3):139), hepatic diseases, hepatic autoimmune diseases, hepatitis, chronic active hepatitis (Franco A. et al., Clin Immunol Immunopathol 1990 March; 54 (3):382), biliary cirrhosis, primary biliary cirrhosis (Jones D E. Clin Sci (Colch) 1996 November; 91 (5):551), nephric diseases, nephric autoimmune diseases, nephritis, interstitial nephritis (Kelly C J. J Am Soc Nephrol 1990 August; 1 (2):140), connective tissue diseases, ear diseases, autoimmune connective tissue diseases, autoimmune ear disease (Yoo T J. et al., Cell Immunol 1994 August; 157 (1):249), disease of the inner ear (Gloddek B. et al., Ann N Y Acad Sci 1997 Dec. 29; 830:266), skin diseases, cutaneous diseases, dermal diseases, bullous skin diseases, pemphigus vulgaris, bullous pemphigoid and pemphigus foliaceus.

Examples of delayed type hypersensitivity include, but are not limited to, contact dermatitis and drug eruption.

Examples of types of T lymphocyte mediating hypersensitivity include, but are not limited to, helper T lymphocytes and cytotoxic T lymphocytes.

Examples of helper T lymphocyte-mediated hypersensitivity include, but are not limited to, $T_h1$ lymphocyte mediated hypersensitivity and $T_h2$ lymphocyte mediated hypersensitivity.

Autoimmune Diseases

Include, but are not limited to, cardiovascular diseases, rheumatoid diseases, glandular diseases, gastrointestinal diseases, cutaneous diseases, hepatic diseases, neurological diseases, muscular diseases, nephric diseases, diseases related to reproduction, connective tissue diseases and systemic diseases.

Examples of autoimmune cardiovascular diseases include, but are not limited to atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), Wegener's granulomatosis, Takayasu's arteritis, Kawasaki syndrome (Praprotnik S. et al., Wien Klin Wochenschr 2000 Aug. 25;1 12 (15-16):660), anti-factor VIII autoimmune disease (Lacroix-Desmazes S. et al., Semin Thromb Hemost.2000; 26 (2): 157), necrotizing small vessel vasculitis, microscopic polyangiitis, Churg and Strauss syndrome, pauci-immune focal necrotizing and crescentic glomerulonephritis (Noel L H. Ann Med Interne (Paris). 2000 May; 151 (3):178), antiphospholipid syndrome (Flamholz R. et al., J Clin Apheresis 1999; 14 (4):171), antibody-induced heart failure (Wallukat G. et al., Am J Cardiol. 1999 Jun. 17; 83 (12A):75H), thrombocytopenic purpura (Moccia F. Ann Ital Med Int. 1999 April-June; 14 (2):114; Semple J W. et al., Blood 1996 May 15; 87 (10):4245), autoimmune hemolytic anemia (Efremov D G. et al., Leuk Lymphoma 1998 January; 28 (3-4):285; Sallah S. et al., Ann Hematol 1997 March; 74 (3):139), cardiac autoimmunity in Chagas' disease (Cunha-Neto E. et al., J Clin Invest 1996 Oct. 15; 98 (8):1709) and anti-helper T lymphocyte autoimmunity (Caporossi A P. et al., Viral Immunol 1998; 11 (1):9).

Examples of autoimmune rheumatoid diseases include, but are not limited to rheumatoid arthritis (Krenn V. et al., Histol Histopathol 2000 July; 15 (3):791; Tisch R, McDevitt H O. Proc Natl Acad Sci units S A 1994 Jan. 18; 91 (2):437) and ankylosing spondylitis (Jan Voswinkel et al., Arthritis Res 2001; 3 (3): 189).

Examples of autoimmune glandular diseases include, but are not limited to, pancreatic disease, Type I diabetes, thyroid disease, Graves' disease, thyroiditis, spontaneous autoimmune thyroiditis, Hashimoto's thyroiditis, idiopathic myxedema, ovarian autoimmunity, autoimmune anti-sperm infertility, autoimmune prostatitis and Type I autoimmune polyglandular syndrome. Diseases include, but are not limited to autoimmune diseases of the pancreas, Type 1 diabetes (Castano L. and Eisenbarth G S. Ann. Rev. Immunol. 8:647; Zimmet P. Diabetes Res Clin Pract 1996 October; 34 Suppl: S125), autoimmune thyroid diseases, Graves' disease (Orgiazzi J. Endocrinol Metab Clin North Am 2000 June; 29 (2):339; Sakata S. et al., Mol Cell Endocrinol 1993 March; 92 (1):77), spontaneous autoimmune thyroiditis (Braley-Mullen H. and Yu S, J Immunol 2000 Dec. 15; 165 (12):7262), Hashimoto's thyroiditis (Toyoda N. et al., Nippon Rinsho 1999 August; 57 (8):1810), idiopathic myxedema (Mitsuma T. Nippon Rinsho. 1999 August; 57 (8):1759), ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), autoimmune prostatitis (Alexander R B. et al., Urology 1997 December; 50 (6):893) and Type I autoimmune polyglandular syndrome (Hara T. et al., Blood. 1991 Mar. 1; 77 (5):1127).

Examples of autoimmune gastrointestinal diseases include, but are not limited to, chronic inflammatory intestinal diseases (Garcia Herola A. et al., Gastroenterol Hepatol. 2000 January; 23 (1):16), celiac disease (Landau Y E. and Shoenfeld Y. Harefuah 2000 Jan. 16; 138 (2):122), colitis, ileitis and Crohn's disease.

Examples of autoimmune cutaneous diseases include, but are not limited to, autoimmune bullous skin diseases, such as, but are not limited to, pemphigus vulgaris, bullous pemphigoid and pemphigus foliaceus.

Examples of autoimmune hepatic diseases include, but are not limited to, hepatitis, autoimmune chronic active hepatitis (Franco A. et al., Clin Immunol Immunopathol 1990 March; 54 (3):382), primary biliary cirrhosis (Jones D E. Clin Sci (Colch) 1996 November; 91 (5):551; Strassburg C P. et al., Eur J Gastroenterol Hepatol. 1999 June; 11 (6):595) and autoimmune hepatitis (Manns M P. J Hepatol 2000 August; 33 (2):326).

Examples of autoimmune neurological diseases include, but are not limited to, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83; Oshima M. et al., Eur J Immunol 1990 December; 20 (12):2563), neuropathies, motor neuropathies (Komberg A J. J Clin Neurosci. 2000 May;7 (3):191); Guillain-Barre syndrome and autoimmune neuropathies (Kusunoki S. Am J Med Sci. 2000 April; 319 (4):234), myasthenia, Lambert-Eaton myasthenic syndrome (Takamori M. Am J Med Sci. 2000 April; 319 (4):204); paraneoplastic neurological diseases, cerebellar atrophy, paraneoplastic cerebellar atrophy and stiff-man syndrome (Hiemstra H S. et al., Proc Natl Acad Sci units S A 2001 Mar. 27; 98 (7):3988); non-paraneoplastic stiff man syndrome, progressive cerebellar atrophies, encephalitis, Rasmussen's encephalitis, amyotrophic lateral sclerosis, Sydeham chorea, Gilles de la Tourette syndrome and autoimmune polyendocrinopathies (Antoine J C. and Honnorat J. Rev Neurol (Paris) 2000 January; 156 (1):23); dysimmune neuropathies (Nobile-Orazio E. et al., Electroencephalogr Clin Neurophysiol Suppl 1999; 50:419); acquired neuromyotonia, arthrogryposis multiplex congenita (Vincent A. et al., Ann N Y Acad Sci. 1998 May 13;

841:482), neuritis, optic neuritis (Soderstrom M. et al., J Neurol Neurosurg Psychiatry 1994 May; 57 (5):544) and neurodegenerative diseases.

Examples of autoimmune muscular diseases include, but are not limited to, myositis, autoimmune myositis and primary Sjogren's syndrome (Feist E. et al., Int Arch Allergy Immunol 2000 September; 123 (1):92) and smooth muscle autoimmune disease (Zauli D. et al., Biomed Pharmacother 1999 June; 53 (5-6):234).

Examples of autoimmune nephric diseases include, but are not limited to, nephritis and autoimmune interstitial nephritis (Kelly C J. J Am Soc Nephrol 1990 August; 1 (2):140).

Examples of autoimmune diseases related to reproduction include, but are not limited to, repeated fetal loss (Tincani A. et al., Lupus 1998; 7 Suppl 2:S107-9).

Examples of autoimmune connective tissue diseases include, but are not limited to, ear diseases, autoimmune ear diseases (Yoo T J. et al., Cell Immunol 1994 August; 157 (1):249) and autoimmune diseases of the inner ear (Gloddek B. et al., Ann N Y Acad Sci 1997 Dec. 29; 830:266).

Examples of autoimmune systemic diseases include, but are not limited to, systemic lupus erythematosus (Erikson J. et al., Immunol Res 1998; 17 (1-2):49) and systemic sclerosis (Renaudineau Y. et al., Clin Diagn Lab Immunol. 1999 March; 6 (2):156); Chan O T. et al., Immunol Rev 1999 June; 169:107).

Infectious Diseases

Examples of infectious diseases include, but are not limited to, chronic infectious diseases, subacute infectious diseases, acute infectious diseases, viral diseases, bacterial diseases, protozoan diseases, parasitic diseases, fungal diseases, mycoplasma diseases and prion diseases.

Graft Rejection Diseases

Examples of diseases associated with transplantation of a graft include, but are not limited to, graft rejection, chronic graft rejection, subacute graft rejection, hyper-acute graft rejection, acute graft rejection and graft versus host disease.

Allergic Diseases

Examples of allergic diseases include, but are not limited to, asthma, hives, urticaria, pollen allergy, dust mite allergy, venom allergy, cosmetics allergy, latex allergy, chemical allergy, drug allergy, insect bite allergy, animal dander allergy, stinging plant allergy, poison ivy allergy and food allergy.

Cancerous Diseases

Examples of cancer include but are not limited to carcinoma, lymphoma, blastoma, sarcoma, and leukemia. Particular examples of cancerous diseases but are not limited to: Myeloid leukemia such as Chronic myelogenous leukemia. Acute myelogenous leukemia with maturation. Acute promyelocytic leukemia, Acute nonlymphocytic leukemia with increased basophils, Acute monocytic leukemia. Acute myelomonocytic leukemia with eosinophilia; Malignant lymphoma, such as Birkitt's Non-Hodgkin's; Lymphocytic leukemia, such as Acute lumphoblastic leukemia. Chronic lymphocytic leukemia; Myeloproliferative diseases, such as Solid tumors Benign Meningioma, Mixed tumors of salivary gland, Colonic adenomas; Adenocarcinomas, such as Small cell lung cancer, Kidney, Uterus, Prostate, Bladder, Ovary, Colon, Sarcomas, Liposarcoma, myxoid, Synovial sarcoma, Rhabdomyosarcoma (alveolar), Extraskeletel myxoid chonodrosarcoma, Ewing's tumor; other include Testicular and ovarian dysgerminoma, Retinoblastoma, Wilms' tumor, Neuroblastoma, Malignant melanoma, Mesothelioma, breast, skin, prostate, and ovarian.

As mentioned hereinabove, the method of this aspect of the present invention is affected by administering to the subject a therapeutically effective amount of CCL2 to thereby treat the inflammation.

As used herein the term "CCL2" refers to a mammalian (e.g., human) CCL2 protein (interchangeably used with polypeptide) or mimetics thereof such as set forth in GenBank Accession Nos. NM_002982 or NP_002973. CCL2 may be synthesized using recombinant DNA techniques or solid phase technology. CCL2 is also commercially available (e.g., Peprotech Inc. Rocky Hill, N.J.). Since the CCL2 of the present invention is used for clinical applications, it is preferably sterile or may be purified of possible contaminating factors (e.g., bacteria, such as by filter).

The CCL2 of the present invention can be administered to the subject per se, or in a pharmaceutical composition where it is mixed with suitable carriers or excipients.

As used herein, a "pharmaceutical composition" refers to a preparation of one or more of the active ingredients described herein (CCL2) with other chemical components such as physiologically suitable carriers and excipients. The purpose of a pharmaceutical composition is to facilitate administration of a compound to the subject.

As used herein, the term "active ingredient" refers to the CCL2 accountable for the intended biological effect.

Hereinafter, the phrases "physiologically acceptable carrier" and "pharmaceutically acceptable carrier," which may be used interchangeably, refer to a carrier or a diluent that does not cause significant irritation to the subject and does not abrogate the biological activity and properties of the administered compound. An adjuvant is included under these phrases.

Herein, the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils, and polyethylene glycols.

Techniques for formulation and administration of drugs may be found in the latest edition of "Remington's Pharmaceutical Sciences," Mack Publishing Co., Easton, Pa., which is herein fully incorporated by reference.

Suitable routes of administration may, for example, include oral, rectal, Tran mucosal, especially Tran nasal, intestinal, or parenteral delivery, including intramuscular, subcutaneous, and intramedullary injections, as well as intrathecal, direct intraventricular, intravenous, inrtaperitoneal, intranasal, or intraocular injections.

Alternately, one may administer the pharmaceutical composition in a local rather than systemic manner, for example, via injection of the pharmaceutical composition directly into a tissue region of a patient.

Pharmaceutical compositions of the present invention may be manufactured by processes well known in the art, e.g., by means of conventional mixing, dissolving, granulating, dragee-making, levigating, emulsifying, encapsulating, entrapping, or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations that can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries as desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, and sodium carbomethylcellulose; and/or physiologically acceptable polymers such as polyvinylpyrrolidone (PVP). If desired, disintegrating agents, such as cross-linked polyvinyl pyrrolidone, agar, or alginic acid or a salt thereof, such as sodium alginate, may be added.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions that can be used orally include push-fit capsules made of gelatin, as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate, and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane, or carbon dioxide. In the case of a pressurized aerosol, the dosage may be determined by providing a valve to deliver a metered amount. Capsules and cartridges of, for example, gelatin for use in a dispenser may be formulated containing a powder mix of the compound and a suitable powder base, such as lactose or starch.

The pharmaceutical composition described herein may be formulated for parenteral administration, e.g., by bolus injection or continuous infusion. -Formulations for injection may be presented in unit dosage form, e.g., in ampoules or in multidose containers with, optionally, an added preservative. The compositions may be suspensions, solutions, or emulsions in oily or aqueous vehicles, and may contain formulatory agents such as suspending, stabilizing, and/or dispersing agents.

Pharmaceutical compositions for parenteral administration include aqueous solutions of the active preparation in water-soluble form. Additionally, suspensions of the active ingredients may be prepared as appropriate oily or water-based injection suspensions. Suitable lipophilic solvents or vehicles include fatty oils such as sesame oil, or synthetic fatty acid esters such as ethyl oleate, triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the active ingredients, to allow for the preparation of highly concentrated solutions.

Alternatively, the active ingredient may be in powder form for constitution with a suitable vehicle, e.g., a sterile, pyrogen-free, water-based solution, before use.

The pharmaceutical composition of the present invention may also be formulated in rectal compositions such as suppositories or retention enemas, using, for example, conventional suppository bases such as cocoa butter or other glycerides.

Pharmaceutical compositions suitable for use in the context of the present invention include compositions wherein the active ingredients are contained in an amount effective to achieve the intended purpose. More specifically, a "therapeutically effective amount" means an amount of active ingredients (e.g., CCL2) effective to prevent, alleviate, or ameliorate symptoms of a disorder (e.g., allergy) or prolong the survival of the subject being treated. The therapeutically effective amount of CCL2 of the present invention is selected to at least partially inhibit CCR2-dependent cell migration or homing.

Determination of a therapeutically effective amount is well within the capability of those skilled in the art, especially in light of the detailed disclosure provided herein.

For any preparation used in the methods of the invention, the dosage or the therapeutically effective amount can be estimated initially from in vitro and cell culture assays (e.g., migration assay as further described hereinbelow). For example, a dose can be formulated in animal models (as shown in the Examples section below, other models of allergy for example include skin allergy and conjunctivitis induced by compound 48/80, see PCT WO 00/78346) to achieve a desired concentration or titer. Such information can be used to more accurately determine useful doses in humans.

Calculations of dosage in mass per kg, for manufactured drugs and supplements, can be made on the basis of conversion of animal doses to human equivalent doses (HED), based on body surface area, as published by the FDA [Guidance for industry and reviewers, estimating the safe starting dose in clinical trials for therapeutics in adult healthy volunteers; website: http://wwwdotfdadotgov/cber/guidelinesdothtm]. See Table 1 below.

TABLE 1

| Species | To convert animal dose in mg/kg to dose in mg/m$^2$, multiply by km below: | To convert animal dose in mg/kg to HED$^a$ in mg/kg, either: Divide animal dose by: | Multiply Animal dose by: |
| --- | --- | --- | --- |
| Human | 37 | — | — |
| Child (20 kg)$^b$ | 25 | — | — |
| Mouse | 3 | 12.3 | 0.08 |

TABLE 1-continued

| Species | To convert animal dose in mg/m², multiply by km below: | To convert animal dose in mg/kg to HED$^a$ in mg/kg, either: Divide animal dose by: | Multiply Animal dose by: |
|---|---|---|---|
| Hamster | 5 | 7.4 | 0.13 |
| Rat | 6 | 6.2 | 0.16 |
| Ferret | 7 | 5.3 | 0.19 |
| Guinea pig | 8 | 4.6 | 0.22 |
| Rabbit | 12 | 3.1 | 0.32 |
| Dog | 20 | 1.8 | 0.54 |
| Primates: | | | |
| Monkeys$^c$ | 12 | 3.1 | 0.32 |
| Marmoset | 6 | 6.2 | 0.16 |
| Squirrel monkey | 7 | 5.3 | 0.19 |
| Baboon | 20 | 1.8 | 0.54 |
| Micro-pig | 27 | 1.4 | 0.73 |
| Mini-pig | 35 | 1.1 | 0.95 |

Hence, according to Table 1 above, an effective dosage given to mice was 60 ng CCL2 per day, as described in Example 2 of the Examples section. The effective dosage of the present invention was therefore 2.4 µg CCL2/Kg body weight (for mouse weight: 25 gr). Thus, considering that the mouse body weight ranges between 11-34 gr, and considering normal human weights is assumed to be 70 kg, HED is achieved by multiplying the dosage given to mouse by 0.081, resulting in 0.2 µg/Kg body weight. Therefore, for the standard human weight range of 50-100 Kg, the dose given would be 10-20 µg CCL2 per day. For weights outside the standard ranges, HED can be calculated by the formula: HED =(animal dose in mg/Kg)×[(animal weight in Kg)/(human weight in Kg)]$^{0.33}$.

Alternatively, calculations can be done with respect to blood volume [see Bussi S, and Morisetti A., Safety margins of intravascular contrasts Arh Hig Rada Toksikol 56:157-160, (2005)], where average mouse blood volume is 2-4 ml, and average human blood volume is 5 L. Since the effective dosage given to mice in the present invention was 60 ng/2-5 ml=15-30 µg/L blood volume, an effective CCL2 dosage administered to humans would be 75-150 µg per day. Dosage for children and animals can be calculated accordingly [Bussi S, and Morisetti A., Safety margins of intravascular contrasts Arh Hig Rada Toksikol 2005; 56:157-160, 2004].

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration, and dosage can be chosen by the individual physician in view of the patient's condition (See, e.g., Fingl, E. et al. (1975), "The Pharmacological Basis of Therapeutics," Ch. 1, p.1).

Dosage amount and administration intervals may be adjusted individually to provide sufficient plasma or brain levels of the active ingredient to induce or suppress the biological effect (i.e., minimally effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks, or until cure is effected or diminution of the disease state is achieved.

The amount of a composition to be administered will, of course, be dependent on the subject being treated, the severity of the affliction, the manner of administration, the judgment of the prescribing physician, etc.

According to the present invention CCL2 is administered at levels such as, but not limited to about 1 ng-100 µgr, about 10 ng-100 µgr, about 100 ng-100 µgr, about 100 ng-300 ng, about 1 µg-100 µg, about 1 ng-50 ng, about 1 ng-200 ng, about 1 ng -300 ng, about 1 ng-500 ng or about 1 ng-1 µgr, per Kg body weight per day, to treat inflammation in accordance with the present invention.

Regardless of the above, CCL2 is administered at an amount selected to avoid unwanted side-effects associated with elevated concentrations of CCL2 (e.g., up-regulated immune response).

CCL2 of the present invention can be formulated in a dosage unit such as for oral administration or rectal administration, or for injection. Such a dosage unit form can comprise, for example about 1 ng-100 µgr, about 1 ng-200 µgr, about 10 ng-100 µgr, about 100 ng-100 µgr, about 100 ng-300 ng, about 1 µg-100 µg, about 1 ng-50 ng, 1 ng-200 ng, about 1 ng -300 ng, about 1 ng-500 ng or about 1 ng-1 µgr, per Kg body weight per day of CCL2.

Compositions of the present invention may, if desired, be presented in a pack or dispenser device, such as an FDA-approved kit, which may contain one or more unit dosage forms containing the active ingredient. The pack may, for example, comprise metal or plastic foil, such as a blister pack. The pack or dispenser device may be accompanied by instructions for administration. The pack or dispenser device may also be accompanied by a notice in a form prescribed by a governmental agency regulating the manufacture, use, or sale of pharmaceuticals, which notice is reflective of approval by the agency of the form of the compositions for human or veterinary administration. Such notice, for example, may include labeling approved by the U.S. Food and Drug Administration for prescription drugs or of an approved product insert. Compositions comprising a preparation of the invention formulated in a pharmaceutically acceptable carrier may also be prepared, placed in an appropriate container, and labeled for treatment of an indicated condition, as further detailed above.

The present findings place CCL2 as an important anti-migration factor which may be used in various culture assays such as employed for identifying migration-modulation agents, and for analyzing cellular phenotypes (aggressiveness/invasiveness).

Thus, according to another aspect of the present invention there is provided a method of regulating cell migration. The method is effected by contacting the cell with a medium comprising an amount of CCL2 selected to inhibit cell migration, thereby regulating cell migration.

As used herein the cell refers to any cell which expresses CCR2 (e.g., cancer cell, immune cell such as T-cells).

The method of this aspect of the present invention may be affected in migration chambers such as described in the Examples section which follows, preferably minutarized for high throughput analysis. Cells may be visualized by microscopy, which may adapt for automatic detection (CCD camera).

CCL2 may be placed in a culture medium suitable for cell growth.

A pro-migration factor may be placed in the same chamber or a parallel one and serve as control (e.g., SDF).

Thus, the present invention provides for the first time a novel tool, CCL2, for down-regulating cell migration. As effectively shown in here, CCL2 may be used to inhibit inflammation, such as associated with allergy.

As used herein the term "about" refers to ±10%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes 1-111 Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Low Levels of CCL2 Downregulate Cytoskeleton Rearrangement and Migration of Naïve T Cells In Vitro To determine the role of the CCR2/CCL2 interaction in the integrin-mediated adhesion and migration of T cells and whether they can regulate the homing of these cells to the lymph nodes (LN) and sites of inflammation in-vivo, expression of CCR2 in T cells was determined by PCR. CCL2 effect on T cell migration and cytoskeleton rearrangement was determined by a Transwell migration assay and an actin polymerization assay Materials and Experimental Procedures Animals—Six to eight week old C57BL/6 or Balb/c mice were used. All animal procedures were approved by the Animal Research Committee at the Weizmann Institute of Science, Rehovot, Israel.

T cell sorting—Spleen and spleen cells were obtained from mice as previously described [Shachar I. and Flavell R. A., Science 274:106 (1996)]. T cells were enriched using the MACS system (Miltenyi Biotec, Auburn, Calif.) according to the manufacturer's protocol. Spleen cells were incubated with anti-CD45R (B220) magnetic beads (Miltenyi Biotec, Auburn, Calif.) and the CD45 negative cells were collected. CD8+ T cells were purified using anti-CD8 magnetic beads (Miltenyi Biotec, Auburn, Calif.). CD4+ T cells were enriched using anti-CD4 magnetic beads (Miltenyi Biotec, Auburn, Calif.). To obtain Th1 and Th2 cells, the T cell enriched population was incubated for 96 hours with concanavalin A (250 µg/ml; Roche, Basel, Switzerland) and IL-12 (3.5 ng/ml; Gibco BRL/Invitrogen, Gaithersburg Md.) for the collection of Th1 cells from the supernatant, or incubated with IL-4 (103 units/ml; Gibco BRL/Invitrogen, Gaithersburg Md.) for the collection of Th2 cells from the supernatant.

RNA isolation and reverse transcription (RT-PCR)—Total RNA was isolated from cells using the Tri reagent kit (MRC). Reverse transcription was carried out using Superscript II RT (Invitrogen, Carlsbad, Calif.) In order to detect expression of CCR2 in different T-cell populations, PCR was conducted on cDNA templates from CD8+, naïve CD4+, or Th1 or Th2 populations of CD4+ cells, using primers specific for CCR2 (forward primer-5'-ATGTTACCTCAGTTCATCCAC-3', SEQ ID NO. 1; reverse primer-5'-GCCCACAAAACCAAA-GATGAAT-3', SEQ ID NO: 2), and primers specific for Hypoxanthine-guanine phosphoribosyltransferase (HPRT) as a positive control (forward primer: 5'-GAGGGTAG-GCTGGCCTATGGCT-3', SEQ ID NO: 3; reverse primer: 5'-GTTGGATACAGGCCAGACTTTGTTG-3', SEQ ID NO: 4).

Stimulation of T cells—Cell stimulation was performed as previously described [Flaishon et al., J Biol Chem. (2001) 276:46701-46706]. Briefly, 1×10$^7$ T cells were suspended in 1 ml DMEM cell medium containing 10% (v/v) Fetal Calf Serum (FCS). Next, 0.1 ng/ml CCL2 (CytoLab) was added to each tube and the tubes were immediately placed in 37° C. for 30 minutes. Immediately after stimulation, cells were washed and handled as described hereinbelow.

Preparation of cell extract—Stimulated cells were lysed in lysis buffer containing: 25 mM Tris, pH 7.4; 2 mM Vanadate; 75 mM glycophosphate, pH 7.2; 2 mM EDTA; 2 mM EGTA; 10 mM NaPPi; and 0.5% NP-40, in the presence of the following protease inhibitors: 10 mg/ml Leupeptin; 10 mg/ml aprotinin; 10 mg/ml pepstatin; 10 mg/ml chymostatin (Roche); 1 mM PMSF (Sigma); and 20 mM N-etheyl-melamide (Sigma).

ERK detection—Cell lysates were separated on a 10% (wt/vol) SDS-PAGE. Proteins were electro-transferred to nitrocellulose membranes and reacted with anti-phospho-specific extracellular signal-regulated kinase (ERK) 1 or 2 (a kind gift from Dr Rony Seger, Weizmann Institute, Rehovot, Israel) followed by peroxidase-labeled goat anti-mouse (Jackson Labs), or reacted with polyclonal anti-Tubulin (Santa Cruz) followed by peroxidase anti-rabbit (Jackson Labs).

Transwell migration assay—Chemotaxis was assayed using Transwell chambers as was previously described [Flaishon, L. F., et al., J. Biol. Chem. 276:46701 (2001)]. Naïve T cells were suspended for 30 minutes with RPMI medium with or without CCL2 (0.1 ng/ml, Peprotech Inc., Rocky Hill, N.J.), and thereafter placed in the upper chamber of a 24 well Transwell plate, and allowed to migrate towards CXCL12 (SDF-1, 0.1 mg/ml PeproTech, Inc., Rocky Hill, N.J.) or to the secondary lymphoid tissue chemokine (SLC, CCL21, 0.4 mg/ml; PeproTech, Inc., Rocky Hill, N.J.), placed in the lower chamber. Following 3 hours, the number of the migrating cells found in the lower chamber was evaluated by FACS (FACS calibur, BD bioscience). Assay was repeated 3 times and results were analyzed as percent migration, being the number of migrating cells in the lower chamber as a fraction of the input cells in the upper chamber.

Cytoskeleton rearrangement—T cells were pre-incubated for 30 minutes in the presence or absence of CCL2 (0.1 ng/ml), and then stimulated with either CXCL12 (0.1 mg/ml PeproTech, Inc., Rocky Hill N.J.), SLC (CCL21, 0.4 mg/ml, PeproTech, Inc., Rocky Hill, N.J.), Rantes (0.1 mg/ml, R&D systems Minneapolis, Minn.), MIP-1β (0.1 mg/ml, R&D systems Minneapolis, Minn.) or Eotoxin (0.1 mg/ml R&D systems Minneapolis, Minn.) for 15 seconds. Cells were then immediately fixed with paraformaldehyde, permeabilized and their intracellular F-actin was stained with FITC-phalloidin (Sigma-Aldrich, St. Louis, Mo.), and then analyzed by flow cytometry to determine the state of their cytoskeleton, as previously described [Flaishon, L. F., et al., J. Biol. Chem. 276:46701 (2001)].

Results

Figure 1A:
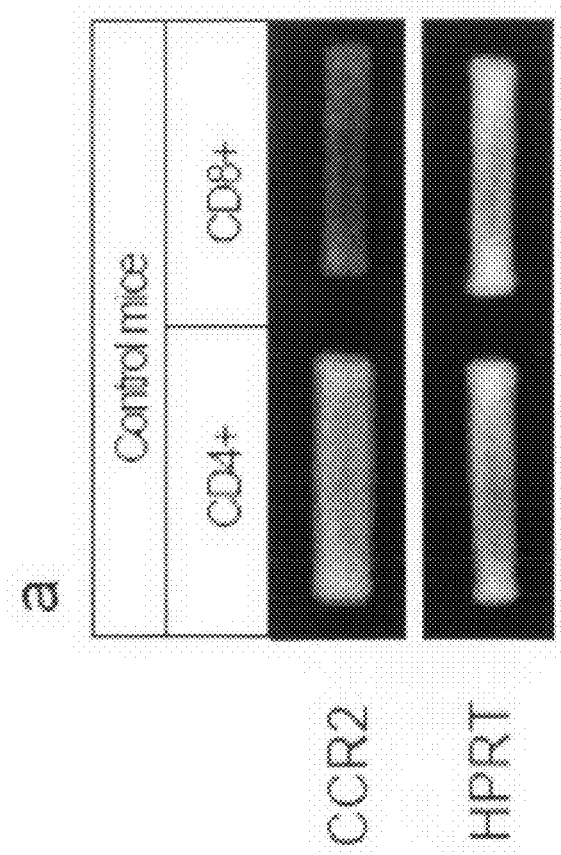

CCR2 is expressed on naïve and effector T cells—Analysis of CCR2 transcription in T cell subsets was effected. Results show that CCR2 mRNA appeared in naïve T cells, and its expression was dramatically higher in the CD4$^+$ T cell population compared to CD8$^+$ T cell population (FIG. 1a). CD4$^+$ T cells that were skewed towards either Th1 or Th2 populations showed CCR2 transcription but at lower levels (FIG. 1b), suggesting that effector T cells express lower levels of CCR2.

Figure 2A:
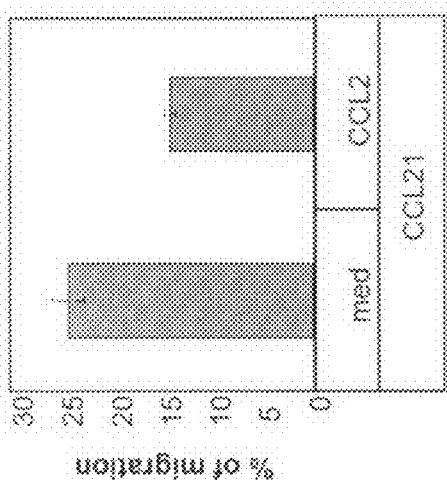
FIGS. 2a-e are bar graphs depicting the inhibitory effect of CCL2 on cytoskeleton rearrangement and migration of naïve T cells.
Figure 2B:
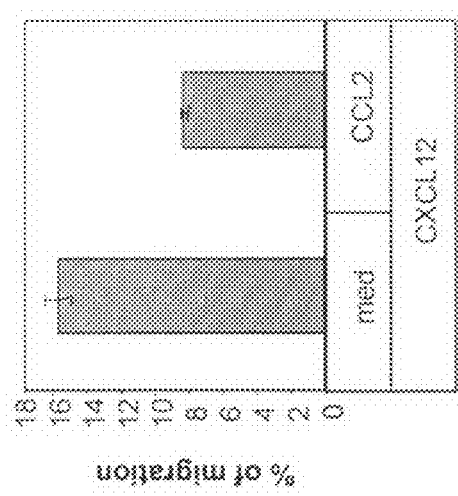

CCL2 inhibits migration of naïve T cells in vitro—To determine whether CCL2 regulates the homing of T cells, the inhibitory effect of CCL2 on T cell migration was examined by a Transwell assay analysis of the migratory response of naïve T cells to the chemokines CXCL12 or SLC. Secondary lymphoid tissue chemokine (SLC, CCL21) is expressed at high levels by high endothelial venules (HEVs) in LNs and functions in recruitment of T cells into LNs [Cyster, J. G. Science 286:2098. (1999)]. CXCL12 (SDF-1) is expressed constitutively by various cells and tissues and serves as a highly efficient and potent chemoattractant for T cells. Results show that low levels of CCL2 inhibited the migration of naïve T cells towards CXCL12 (FIG. 2a) and CCL21 (FIG. 2b) by about 40-50%. These results indicate that low levels of CCL2 are sufficient to inhibit T cell migration.

CCL2 specifically downregulates actin polymerization—Among the requirements for integrin-mediated migration are an increased rate of actin polymerization, and extensive reorganization of the actin-based cytoskeleton.

Figure 2E:
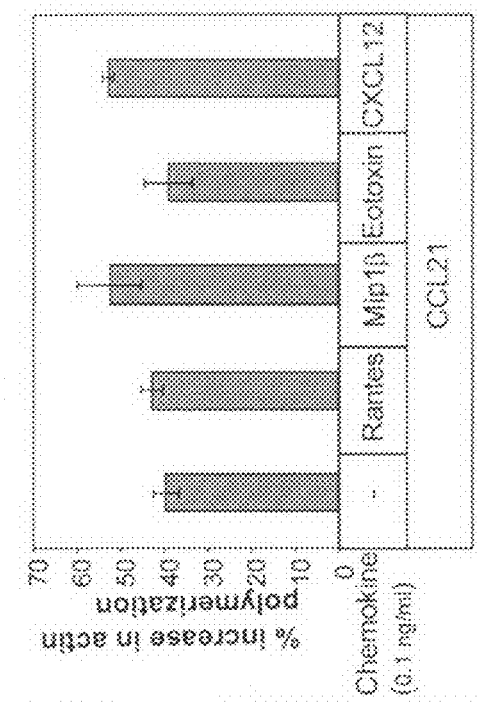
Figure 2D:
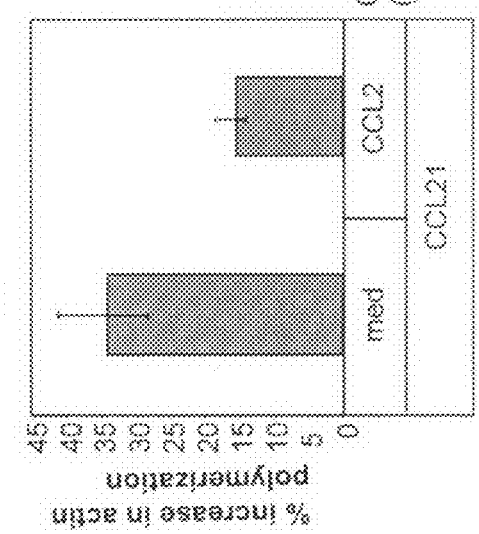
Figure 2C:
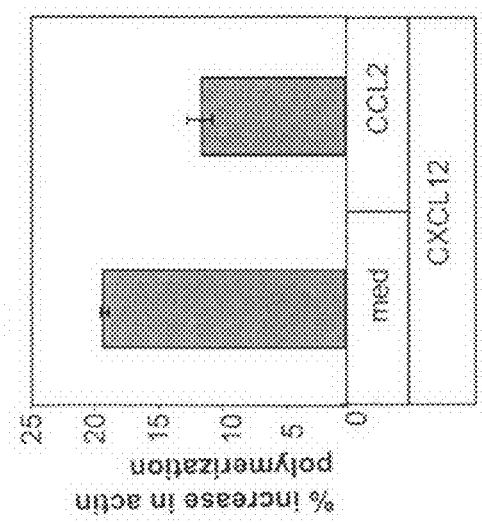

To determine whether CCL2 regulates the cytoskeletal rearrangement of T cells, the actin polymerization of naïve T cells was followed. As shown in FIGS. 2c-d, CXCL12 (FIG. 2c) or CCL21 (FIG. 2d) stimulation indeed induced actin polymerization, which was inhibited by about 40-50% in cells pre-treated with CCL2.

To evaluate whether additional chemokines (at pM concentrations) have an inhibitory effect on T cell cytoskeletal rearrangement, the actin polymerization of naïve T cells was followed following subjection to various chemokines. As shown in FIG. 2e, low levels of Rantes, Mip1β, Eotoxin or CXCL12 had no inhibitory effect on the actin polymerization of naïve T cells.

Figure 3:
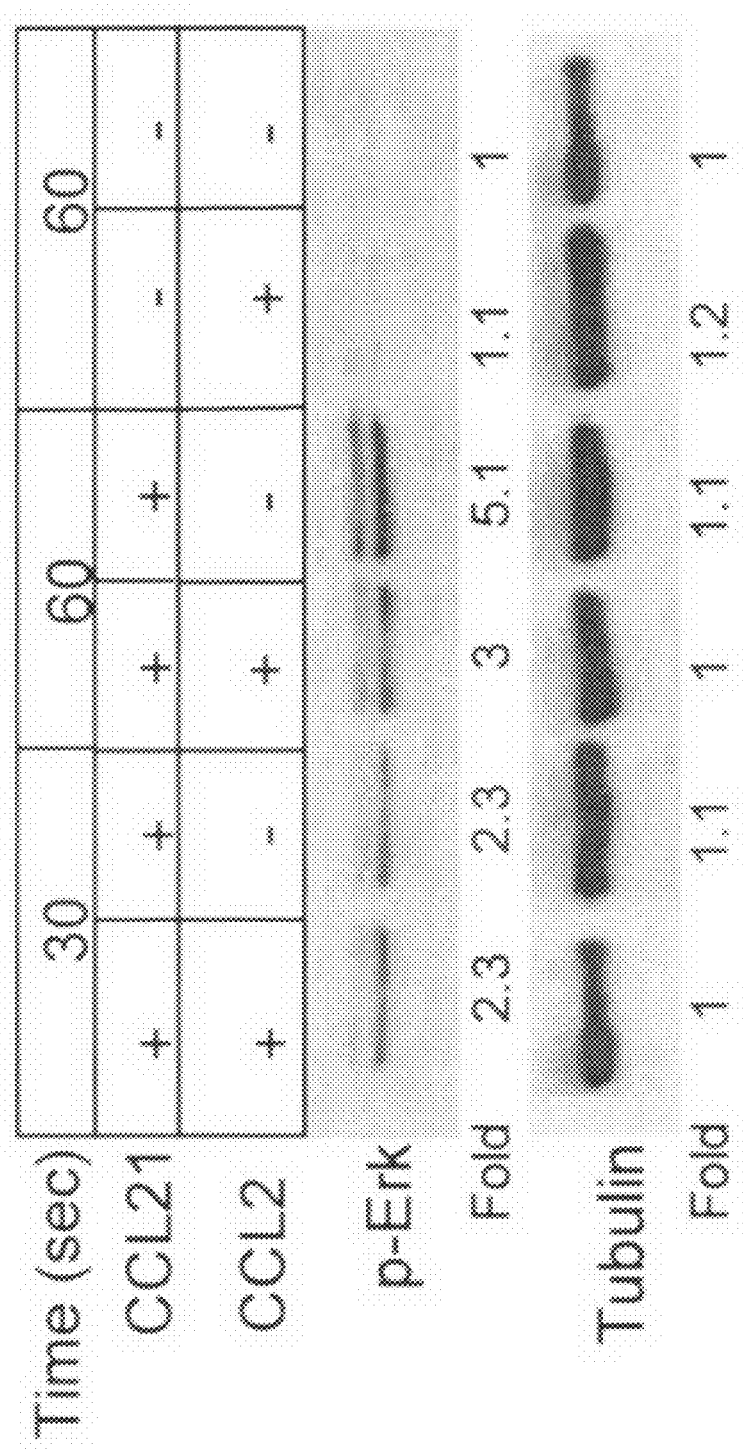
FIG. 3 is a graph depicting CCL2 inhibition of ERK phosphorylation. Naïve T cells were pre treated with CCL2 for 30 minutes and then stimulated for 30 or 60 seconds by CCL21, cells were washed, lysed and separated by SDS-PAGE (as described in detail in Example 1). Proteins were electrotransferred to nitrocellulose membranes and reacted with anti-phospho-ERK followed by peroxidase-labeled goat anti-mouse, or reacted with polyclonal anti-Tubulin followed by peroxidase anti-rabbit.

Inventors have previously shown that activation of ERK½ was inhibited when immature B cells were pretreated with CCL2 [Flaishon et al., Blood (2004) 104: 933-941]. Therefore, inventors wanted to determine whether CCL2 inhibited ERK phosphorylation in T cells as well. As can be seen in FIG. 3, CCL21 induced phosphorylation of ERK½. This activation was inhibited in cells pre-treated with CCL2. Thus, CCL2 regulates a signaling cascade that involves ERK ½ resulting in inhibition of cytoskeleton rearrangement and migration.

Taken together, these results suggest that the CCR2/CCL2 interaction controls the integrin-mediated adhesion and migration of T cells. CCL2 was shown to inhibit the migration of T cells by down-regulating their ability to polymerize actin in a signaling pathway that involves ERK ½.

Example 2

CCL2 Inhibits Naïve T Cells Homing Into Lymph Nodes

The powerful inhibitory effect of CCL2 on CCL21 and CXCL12 chemokine-triggered migration of T-lymphocytes in vitro suggested that this cytokine could also interfere with naïve T cell migration in vivo and homing into lymph nodes (LNs), and thus serve as an anti-inflammatory compound. To determine the in vivo effect of CCL2 on the homing of naïve T cells, T cell entry into the peripheral lymph nodes (PLNs) was analyzed.

Materials and Experimental Procedures

Animals—as detailed in Example 1 hereinabove.

Tracking of cells in vivo—T cells pre-incubated for 30 minutes in the presence or absence of CCL2 (0.1 ng/ml RPMI) were washed, and labeled with 5 mM of the fluorescent dye CFDA-SE (Molecular Probes/Invitrogen, Carlsbad, Calif., USA) for 15 minutes at room temperature. Thereafter, an equal amount (0.33×10$^7$) of CCL2-treated or -untreated cells were injected i.v. into C57BL/6 mice. After 3 hours, LNs and spleens were collected and the FITC-positive population was analyzed by FACS. The proportion of labeled cells recovered in the LN and spleen was determined as previously described [Flaishon, L. R., J. Exp. Med. 192:1381 (2000)] in four different experiments (10 mice in each group).

Results

Figure 4B:
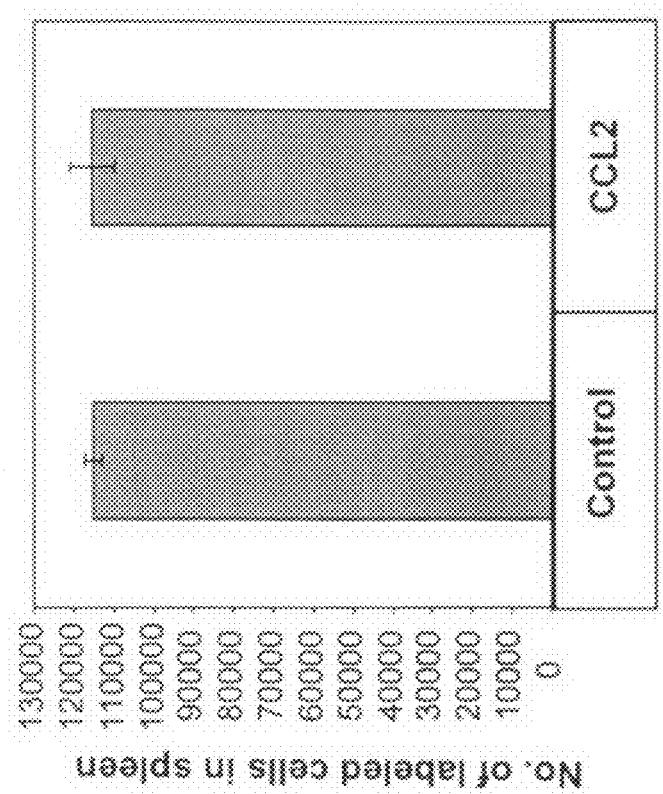
FIGS. 4a-b are bar graphs depicting homing of naive T cells into LNs. An equal amount of T cells incubated with or without CCL2 and labeled with the fluorescent dye CFDA-SE were injected to mice. After 3 hours, the peripheral lymph nodes (PLNs, FIG. 4a) or spleen (FIG. 4b) were collected and the FITC-positive population was analyzed by FACS. The results presented are representative of four different experiments.
Figure 4A:
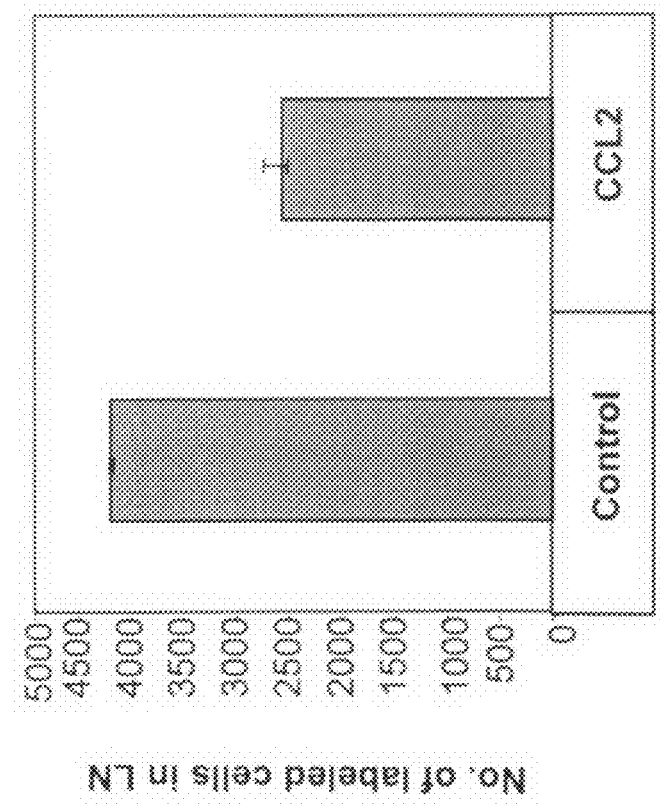

Compared to the control population (treated with PBS), there was a dramatic 50% reduction in the homing of CCL2-treated naïve T cells into the LN (FIG. 4a). Interestingly, there was no difference in the migration of these T cells to the spleen (FIG. 4b). The entry of lymphocytes into the spleen was regarded until recently as a process for which integrin activation was not required [Saito S., Pathobiology (1995) 63: 305; Kraal G., Am. J. Pathol. (1995) 147: 763; Nolte M. A., Immunology (2002) 106:299], but recent results showed that integrin activation also plays a role in the entry of mature B cells into the splenic white pulp [Lo C. G., J. Exp. Med. (2003) 197: 353]. However, while inhibition of a single integrin (e.g., LFA-1) resulted in a dramatic inhibition of homing of T and B cells to the lymph nodes, it had only a minor effect on their entrance to the splenic white pulp and only dual integrin inhibition could inhibit the lymphocyte entrance to the splenic white pulp [Lo C. G., supra]. Thus in conclusion, CCL2 inhibits the migration of naïve T cells into LNs in vivo, possibly due to its suppressor effect on chemokine-induced integrin-mediated adhesion and migration.

Example 3

CCL2 Inhibits LFA-1 Integrin-Mediated Lymphocyte Firm Adhesion to High Endothelial Venule Walls in Mouse Peripheral Lymph Nodes To corroborate the in vitro findings (described in Example 2) in a more physiological setting, the effects of low-dose CCL2 on lymphocyte migration and homing through high endothelial venules (HEVs) in the peripheral lymph nodes (PLNs), microcirculation was employed by intravital microscopy (IVM).

Materials and Experimental Procedures

Animals—Five- to seven-week-old female C57BL/6 mice were purchased from Charles River laboratories (France). Mice were housed and bred in a specific pathogen-free animal facility. Experiments were conducted in accordance with the French procedural guidelines for animal handling.

Intravital microscopy of mouse subiliac LN—Mice were anesthetized by intraperitoneal injection of 1 mg/ml xylazine and 5 mg/ml ketamine. The right femoral artery was catheterized. The left subiliac LN was prepared for IVM as previously described [Carriere et al., Cancer Res. (2005) 65:11639-11648; M'Rini et al., J Exp Med. (2003) 198:1301-1312], and the mouse was then transferred to a customized intravital video microscopy setup (INM 100; Leica Microsystems SA, Rueil-Malmaison, France) equipped with water immersion objectives (HCX APO; Leica Microsystems SA, Rueil-Malmaison, France). Fluorescent events in the LN microcirculation were visualized and recorded by a silicon-intensified target camera (Hamamatsu Photonics, Massy, France) and stored on DVCAM video tapes (DSR-11 Sony, IEC-ASV, Toulouse, France).

For visualization of naive lymphocyte interactions with LN vascular endothelium, naïve lymphocytes obtained from single T and B cell suspensions of a control C57BL/6 pool of subiliac, axillary, brachial and mesenteric LNs were incubated in the presence or absence of CCL2 (R&D Systems, Lille, France; 1 ng/ml, 30 minutes, 37° C.), fluorescently labeled by calcein AM (Molecular Probes-Invitrogen, Cergy Pontoise, France; 0.25 microM, 5 min, 37° C.) and then injected into the right femoral artery. Cell behavior in LN venules was assessed as previously described [Carriere et al., supra; M'Rini et al., supra]. The rolling fraction was determined as the percentage of cells that rolled along the vascular lining in the total flux of cells per venule. The sticking fraction was determined as the percentage in rolling cells of cells firmly adherent for at least 10 seconds or 1 minute.

Results

Figure 5A:
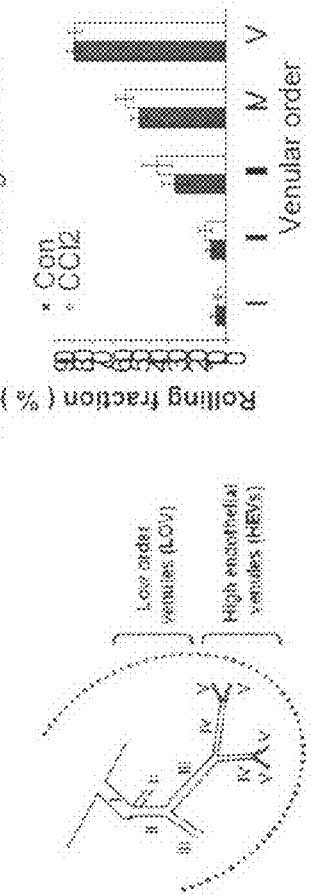
FIGS. 5a-g are graphs depicting inhibition of integrin-mediated lymphocyte firm adhesion to HEV walls in mouse PLNs by CCL2.
Figure 5B:
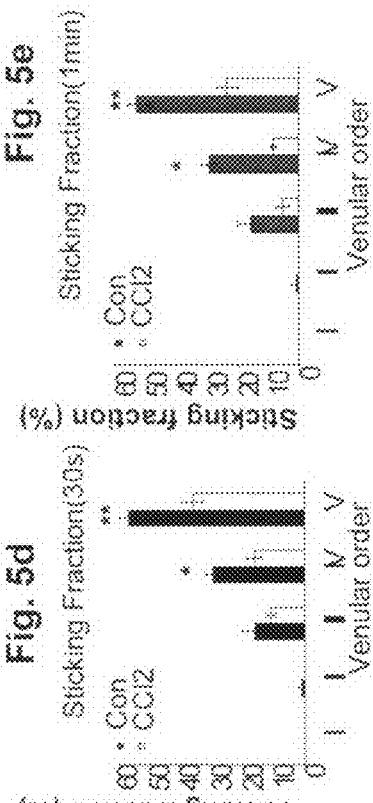
Figure 5C:
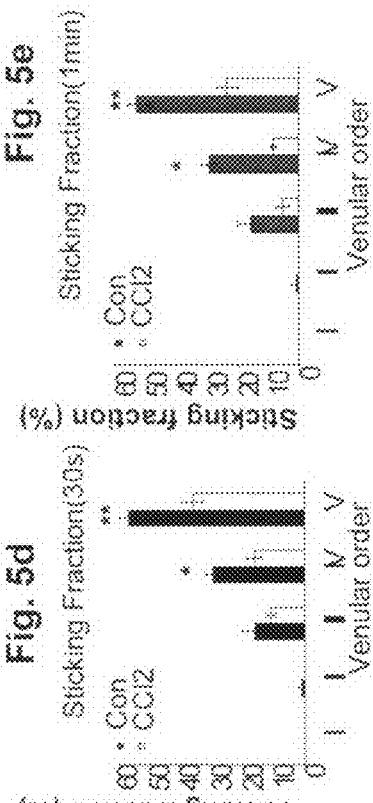
Figure 5D:
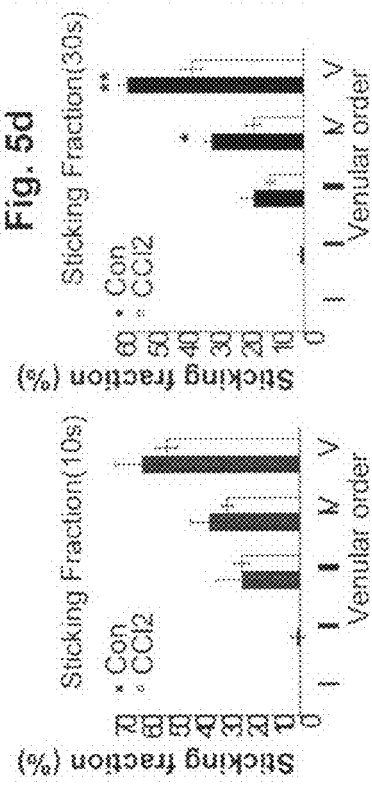
Figure 5E:
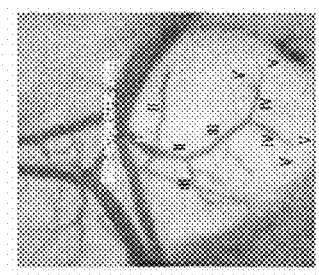
Figure 5F:
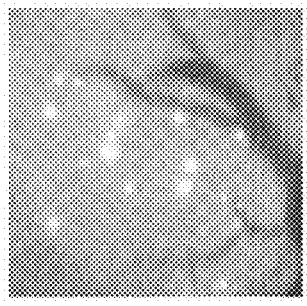
Figure 5G:
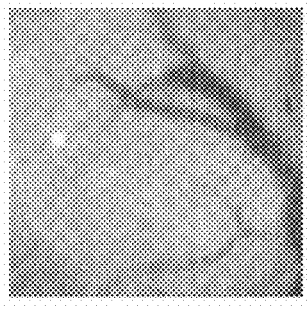

Previous IVM observations of normal murine subiliac LNs have established that the LN venular tree consists of up to five branching orders [Carriere et al., supra; M'Rini et al., supra; von Andrian, Microcirculation. (1996) 3:287-300], where the low order venules (LOVs) comprise a large collecting venule in the hilus (order I) and upstream branches in the medulla (order II and some of order III). The higher order branches (most of order III and all of order IV and V venules) are HEVs directly connected to the LN capillaries and flowing towards the LN sub-and paracortex (FIG. 5a). Analysis of the behavior (e.g., rolling, sticking) of control- and CCL2-treated lymphocytes in the LOVs (order II) and HEVs (orders III, IV and V) was performed. As clear from the results, treatment with low dose CCL2 did not significantly alter the ability of lymphocytes to undergo L-selectin mediated rolling in HEVs (FIG. 5b). Similarly, the percentage of naïve lymphocytes that stuck for at least 10 seconds after rolling inside the HEVs (sticking fraction 10 seconds) was comparable for control- and CCL2-treated lymphocytes (FIG. 5c), indicating that CCL2 pretreatment did not affect the earliest events of CCL21 triggered integrin-mediated arrest in vivo. However, lymphocytes treated with low dose of CCL2 remain arrested only for several seconds in the HEV walls, before detaching, thus leading to a severe reduction in the percentage of cells which remained adherent 30 seconds or 1 minute after their initial arrest (FIGS. 5d and 5e, respectively) when compared to control-lymphocytes. This impairment in the capacity of CCL2-treated lymphocytes to resist detachment by the persistent forces they experience while attached to HEVs resulted in a striking reduction in the number of firmly bound lymphocytes in the PLN venular tree, 30 minutes after injection of the fluorescent cells (FIGS. 5f and 5g). Without the crucial capacity to remain adherent minutes after initial accumulation on the HEV target vessels, lymphocytes would fail to extravasate these vessels. Thus, low dose of CCL2 inhibited integrin-dependent lymphocyte firm adhesion to and extravasation across HEV walls in the mouse PLN microcirculation. Given that mature B cells do not express CCR2 [Flaishon L, et al., supra], it is believed that the dramatic down-regulation observed is mainly of the T cell population.

Example 4

CCL2 Inhibits Post Arrest Integrin-Dependent Adhesion Strengthening of T Lymphocytes on ICAM-1 and VCAM-1 Triggered by Co-Immobilized CCL21

To provide additional mechanistic data about the inhibitory effects of CCL2 on lymphocyte migration and extend the observations to human T cells, analysis was performed in vitro by flow chamber assays with purified components.

Materials and Experimental Procedures

Laminar flow adhesion assays—Purified VCAM-1 or ICAM-1-Fc (both from R&D Systems, Minneapolis, Minn.) were coated with or without CCL21 (R&D Systems) on polystyrene plates as previously described [Grabovsky et al., J Exp Med. (2000) 192:495-506; Sigal et al., J Immunol. (2000) 165:442-452]. The polystyrene plates were each assembled on the lower wall of the flow chamber as previously described [Feigelson et al., J Biol Chem. (2001) 276: 13891-13901]. All flow experiments were conducted at 37° C. Cells were washed with cation-free H/H medium, resuspended in binding medium (H/H medium supplemented with 1 mM $CaCl_2$ and 1 mM $MgCl_2$) and perfused through the flow chamber at low shear stress (0.5-0.75 dyn/cm$^2$) for 2 minutes. Tethers were defined as transient or rolling if cells attached briefly (<2 seconds) to the substrate and as arrests if immediately arrested and remaining stationary for at least 5 seconds of continuous flow. Frequencies of adhesive categories within differently pretreated cells were determined as a percentage of cells flowing immediately over the substrates, as previously described [Grabovsky et al., supra]. To assess resistance to detachment over time, accumulated cells were subjected to a shear stress of 5 dyn/cm$^2$ for 5 minutes. At the indicated time points, the number of cells that remained bound was expressed relative to T cell population originally accumulated in the first 2 minute period of the assay. Over 90% of cellular tethers to VCAM-1 or ICAM-1 were blocked by pretreating cells with VLA-4 or LFA-1 blockers respectively.

Results

An analysis was established to test whether short exposure of human T lymphocytes to low dose CCL2 could impair the ability of the two major T cell integrins, LFA-1 and VLA-4, to undergo activation by in-situ signals from surface bound CCL21. CCL21 when co-immobilized with either ICAM-1 or VCAM-1 triggers robust Gi-mediated LFA-1 or VLA-4 mediated lymphocyte adhesion, respectively under shear flow conditions [Grabovsky et al., supra].

CCL2 treatment of human T cells did not interfere with either LFA-1 or VLA-4 activation on these lymphocytes by surface bound CCL21 as evident from the normal capacity of CCL2 treated T cells to interact with both the LFA-1 and VLA-4 ligands, ICAM-1 and VCAM-1, respectively in the presence of CCL21 (FIGS. 6a and 6c). Nevertheless, once normally captured and arrested on these ligands, in response to CCL21 signals, CCL2 pretreated T cells failed to develop adhesion strengthening and readily detached from their integrin ligands when continuously exposed to high shear stresses (FIGS. 6b and 6d). A similar pretreatment of T lymphocytes with low dose of CXCL12 retained both integrin mediated arrest and subsequent adhesion strengthening under identical conditions (FIGS. 6a-d).

Taken together, these results showed that low dose of CCL2, while not affecting early LFA-1 and VLA-4 activation by in situ CCL21, interferes with crucial cytoskeletal rearrangements triggered by this chemokine at a post arrest step. Without these rearrangements, normally arrested T cells accumulated on both LFA-1 and VLA-4 ligands in response to CCL21 signals failed to develop subsequent adhesion strengthening on these adhesive surfaces when subjected to prolonged application of shear forces.

Example 5

CCL2 Inhibits Effector T Cells Cytoskeleton Rearrangement and Transwell Migration CCR2 transcription in effector CD4$^+$T cells and the inhibitory effect of CCL2 on cytoskeletal rearrangement and migration of effector T cells was analyzed.

Materials and Experimental Procedures

T cell sorting—Spleen and spleen cells were obtained from mice as previously described [Shachar I. and Flavell R. A., Science 274:106 (1996)]. T cells were enriched using the MACS system (Miltenyi Biotec, Auburn, Calif.) according to the manufacturer's protocol. Spleen cells were incubated with anti-CD45R (B220) magnetic beads (Miltenyi Biotec, Auburn, Calif.) and the CD45 negative cells were collected. CD4+ T cells were enriched using anti-CD4 magnetic beads (Miltenyi Biotec, Auburn, Calif.). To obtain Th1 and Th2 cells, the T cell enriched population was incubated for 96 hours with concanavalin A (250 µg/ml; Roche, Basel, Switzerland) and IL-12 (3.5 ng/ml; Gibco BRL/Invitrogen, Gaithersburg Md.) for the collection of Th1 cells from the supernatant, or incubated with IL-4 (103 units/ml; Gibco BRL/Invitrogen, Gaithersburg Md.) for the collection of Th2 cells from the supernatant.

RNA isolation and reverse transcription (RT-PCR)—Total RNA was isolated from cells using the Tri reagent kit (MRC). Reverse transcription was carried out using Superscript II RT (Invitrogen, Carlsbad, Calif.) In order to detect expression of CCR2 in different T-cell populations, PCR was conducted on cDNA templates from Th1 or Th2 populations of CD4+ cells, using primers specific for CCR2 (forward primer-5'-ATGT-TACCTCAGTTCATCCAC-3', SEQ ID NO. 1; reverse primer-5'-GCCCACAAAACCAAAGATGAAT-3', SEQ ID NO: 2), primers specific for Hypoxanthine-guanine phosphoribosyltransferase (HPRT) as a positive control (forward primer: 5'-GAGGGTAGGCTGGCCTATGGCT-3', SEQ ID NO: 3; reverse primer: 5'-GTTGGATACAGGCCA-GACTTTGTTG-3', SEQ ID NO: 4), primers specific for T-bet (forward primer: 5'-TTCCCATTCCTGTCCT-TCACCG-3', SEQ ID NO: 5; reverse primer: 5'-GGAAG-GTCGGGGTAAAAAC-3', SEQ ID NO: 6) and primers specific for GATA-3 (forward primer: 5'-TCTGGAGGAAACGCTAATGG-3, SEQ ID NO: 7; reverse primer: 5'-GAACTCTTCGCACACTTG-GAGACTC-3', SEQ ID NO: 8).

Cytoskeleton rearrangement—T cells were pre-incubated for 30 minutes in the presence or absence of CCL2 (0.1 ng/ml), and then stimulated with either CXCL12 (0.1 mg/ml PeproTech, Inc., Rocky Hill N.J.) or SLC (CCL21, 0.4 mg/ml, PeproTech, Inc., Rocky Hill, N.J.), for 15 seconds. Cells were then immediately fixed with paraformaldehyde, permeabilized and their intracellular F-actin was stained with FITC-phalloidin (Sigma-Aldrich, St. Louis, Mo.), and then analyzed by flow cytometry to determine the state of their cytoskeleton, as previously described [Flaishon, L. F., et al., J. Biol. Chem. 276:46701 (2001)].

Results

CD4$^+$ T cells were skewed towards either Th1 or Th2 populations. Both populations were found to transcribe CCR2, while transcription factors T-bet and GATA-3 showed preferential expression in Th1 and Th2 T cells, respectively (FIGS. 7A).

Furthermore, low dose CCL2 down-regulated the CCL21 (FIGS. 7b and 7d) or CXCL12 (FIGS. 7c and 7e) induced cytoskeleton rearrangement and transwell migration (data not shown) of effector cells, showing that pM levels of CCL2 negatively regulate migration of naïve and effector T cells. Thus, low dose CCL2 exhibits similar inhibitory effects on Th1, Th2 and naïve T cell adhesion and migration.

Example 6

CCL2 Plays an Anti-Inflammatory Role In Vivo

The powerful inhibitory effect of CCL2 on chemokine triggered migration and integrin-dependent adhesion of T-lymphocytes in vitro and in vivo suggested that this cytokine might serve as an anti-inflammatory compound. To determine in vivo the anti-inflammatory effect of CCL2, a mouse asthma model, a rheumatoid arthritis rat model and inflammatory bowel disease mouse model were effected.

Materials and Experimental Procedures

Animals—C57BL/6 or Balb/c mice were used at 6-8 weeks of age. Female Lewis rats were raised and maintained under pathogen-free conditions in the Animal Breeding Center. All animal procedures were approved by the Animal Research Committee at the Weizmann Institute.

Ovalbumin (OVA) sensitization, challenge and treatment with CCL2—OVA sensitization and challenge were effected following a previously described protocol [Flaishon, L., et al., J. Immunol: Cutting edge 168: 3707 (2002)], BALB/c mice (average: 9 mice/group) were sensitized for OVA by intraperitoneal injections with 100 μg of chicken egg ovalbumin (OVA; Sigma-Aldrich, St. Louis, Mo.) mixed with 2 mg of aluminum hydroxide (Pierce, Rockford, Ill.) in 300 μl PBS (control group mice were injected with PSB alone). Injections were given on day 0, 7, and 14. 15 days after initial sensitization, and following, animals were challenged daily for 5 days (days 15-19) by inhaling 4% OVA in PBS, administered by an ultrasonic nebulizer (DeVilbiss, Somersel, Pa.) for 20 minutes, while the control group was challenged with PBS alone.

One of the groups injected and challenged by OVA was additionally injected i.p. with 300 μl PBS from the first day of OVA inhalation (day 15), for 5 days 20 minutes before each inhalation, and another group was additionally injected with murine CCL2 (60 ng CCL2 per animal per day). PBS-treated control group was PBS challenged and PBS injected. On day 18, 2 hours following inhalation, mice were anesthetized by an i.p. injection of 0.2 ml Ketamine/xylazine, and airway hyper-responsiveness (AHR) was determined by calculating the enhanced respiratory pause (Penh), a function of the ratio of peak expiratory flow to peak inspiratory flow and a function of the timing of expiration, measured in a plethysmographic box during expiration. Delta Penh was calculated by subtracting control Penh measurements, before antigen challenge, from the Penh measurements after antigen challenge. Baseline Penh levels were comparable among PBS treated control, OVA-primed mice, and OVA-primed mice, treated with CCL2 on day 15. On day 19 the mice were sacrificed 2 hours after the last inhalation.

Lung histology—Lungs from mice participating in the OVA sensitization and challenge assay were inflated with 1 ml of 10% formalin until distended. Samples for paraffin sectioning were immersed in 10% formalin and fixed for 48 hours. The tissues were then embedded in paraffin and 2-3 micrometer sections were prepared. Hematoxylin/eosin stained sections were examined by light microscopy. Blinded evaluation and scoring (score range: 1-4; based on lymphocyte infiltration and bronchial wall thickness) of lung slides from 9 animals in each group was given by pathologists.

Adjuvant Arthritis (AA) induction, assessment and treatment with CCL2-—AA was induced as previously described [Kannan, Theor Biol Med Model. (2005) 2:17] using 1 mg per rat of heat-killed Mt strain H37Ra (Difco). Each experimental and control group included at least eight rats. The day of AA induction was designated as day 0 and disease severity was assessed by direct observation of all four limbs in each animal. An observer blind to the experimental procedure scored AA for clinical manifestation of disease. A relative score between 0 and 4 was assigned to each limb, based on the degree of joint inflammation, redness and deformity. The maximum possible score for an individual animal was 16 [Kannan, supra].

Immediately following AA induction, rats were divided into two groups that were injected daily (from day 0 to day 5) with low dose CCL2 (240 ng in 300 μl of PBS) or PBS as control. Starting from day 10 post induction, the disease was scored as described hereinabove.

Results were presented as the mean±SEM of the difference between the two values for all the animals in each group. Experiments were repeated at least three times and produced similar results.

TNBS colitis model and treatment with CCL2—TNBS colitis was induced as previously described [Ohkawara et al. (2002) Gastroenterology, 123:256]. Briefly, mice were anesthetized by i.p. injection (35 μl per mouse) of a mixture containing 85% ketamine and 15% xylazine (20 mg/ml). Next, 100 μl of TNBS [55% volume of 50% ethanol mixed with 45% volume of TNBS solution (trinitrobenzene sulfuric acid; Sigma-Aldrich)] was infused into the colonic lumen (about 3.5 cm of the anal verge) via 1 ml syringe attached to a feeding needle. Treated mice were weighted daily and visually inspected for clinical symptoms, such as rectal bleeding and diarrhea.

TNBS mice were divided into 6 groups. CCL2 groups (10 mice in each group) were injected i.p. daily with different CCL2 concentrations (30 ng, 60 ng or 180 ng) in 200 μl of PBS from day 0 (immediately after TNBS induction) to day 6. Control groups (10 mice in each group) were injected i.p. daily with 200 μl PBS alone. Additionally, 5 mice were injected i.p. daily with dexamethasone; and 1 mouse which was not treated and served as negative control for future histology and weight.

Macroscopic and histological assessment of colitis—An observer blind to the experimental procedure scored colitis for clinical manifestation of disease. The colon was macroscopically examined (×5 magnification) to evaluate the macroscopic lesions according to the Wallace criteria. The Wallace score ranks macroscopic colon lesions on a scale from 0 to 16 based on criteria reflecting inflammation, such as hyperemia, thickening of the bowel and the extent of ulceration. The colon was cut lengthwise and fixed in 4% paraformaldehyde for future histology.

Statistical Analysis—For statistical comparison of paired samples, a two-tailed Student's t test was used. Differences were considered statistically significant when $P<0.05$ (*), $P<0.01$ () or $P<0.001$ (*). Data are presented as mean±SEM.

Results

CCL2 plays an anti-inflammatory role in an asthma model—To examine the possible anti-inflammatory effect of CCL2 on allergic airway reactivity, a treatment assay using OVA sensitization, and its response to intraperitoneal injection of CCL2, beginning on the first day of ovalbumin (OVA) inhalation, was effected. The airway responsiveness of anesthetized, spontaneously breathing mice was evaluated 5 days after OVA inhalations. As shown in FIG. 8a, the OVA-challenged mice significantly increased their airway responsiveness to the antigen challenge. However, no airway hyperactivity was observed in control (PBS-challenged) mice, or in OVA-challenged mice treated with CCL2.

Histopathologic examination of lung tissue from OVA treated mice (FIGS. 8b-d) revealed a pleomorphic peribronchial and perivascular infiltrate consisting mainly of eosinophils and lymphocytes (asthmatic mice, FIG. 8c), that was not seen in control PBS-challenged (control mice FIG. 8b) or CCL2-treated mice (CCL2 treated mice FIG. 8d, wherein the small purple dots are cells infiltrating the tissue. In addition, the peribronchial and perivascular inflammatory infiltrates were given inflammatory scores ranging between 1-4 by a pathologist unaware of the differing treatments to which the mice had been exposed (FIG. 8e). The peribronchial inflammatory infiltrate in the OVA-treated mice was significantly increased, as compared to control animals; however, histological changes in the lungs of OVA and CCL2-treated mice were barely detectable, and the inflammatory infiltrate was significantly reduced.

Figure 9:
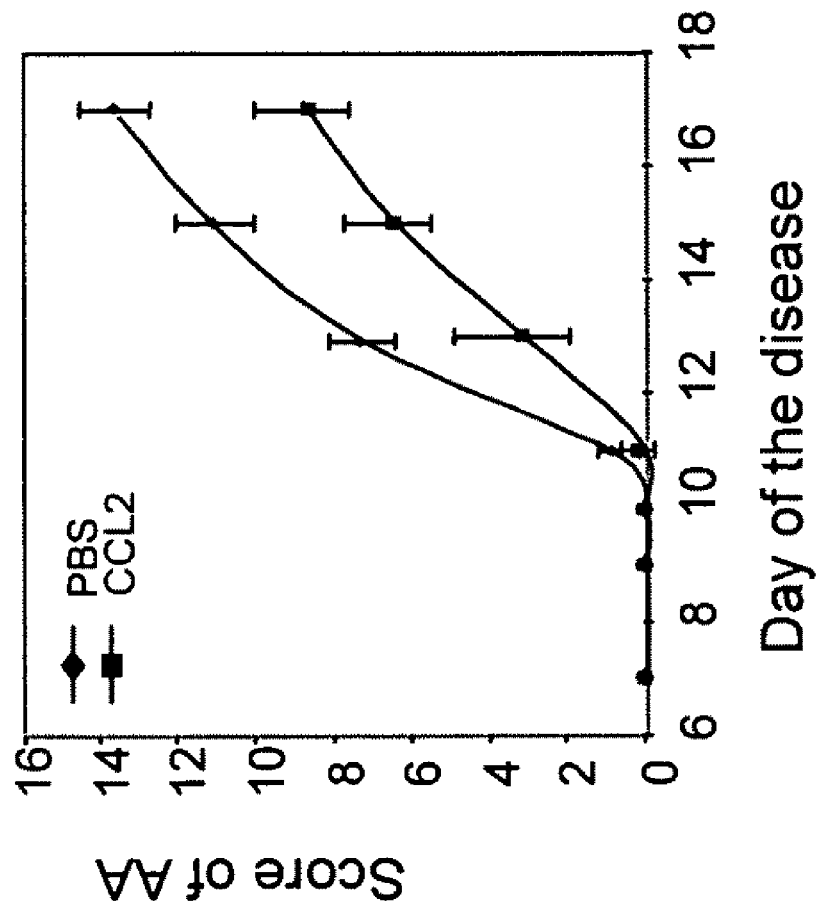
FIG. 9 is a graph depicting the inhibition of adjuvant arthritis (AA) by CCL2 in a rat model. AA was induced in rats as described in Example 6 and grouped according to treatment with low dose CCL2 or PBS. The relative score between 0 and 4 was assigned to each limb, based on the degree of joint inflammation, redness, and deformity; thus the maximum possible score for an individual animal was 16. The graph represents the disease score of 9 animals that were measured every other day.

CCL2 plays an anti-inflammatory role in AA—To examine the possible anti-inflammatory effect of CCL2 on Adjuvant arthritis (AA), the experimental autoimmune disease that models several features of human Rheumatoid Arthritis [Kannan, supra], CCL2 was administered to AA induced rats. As shown in FIG. 9, injection of low dose of CCL2 significantly inhibited the onset of the disease by reducing the severity of the inflammation.

Figure 10:
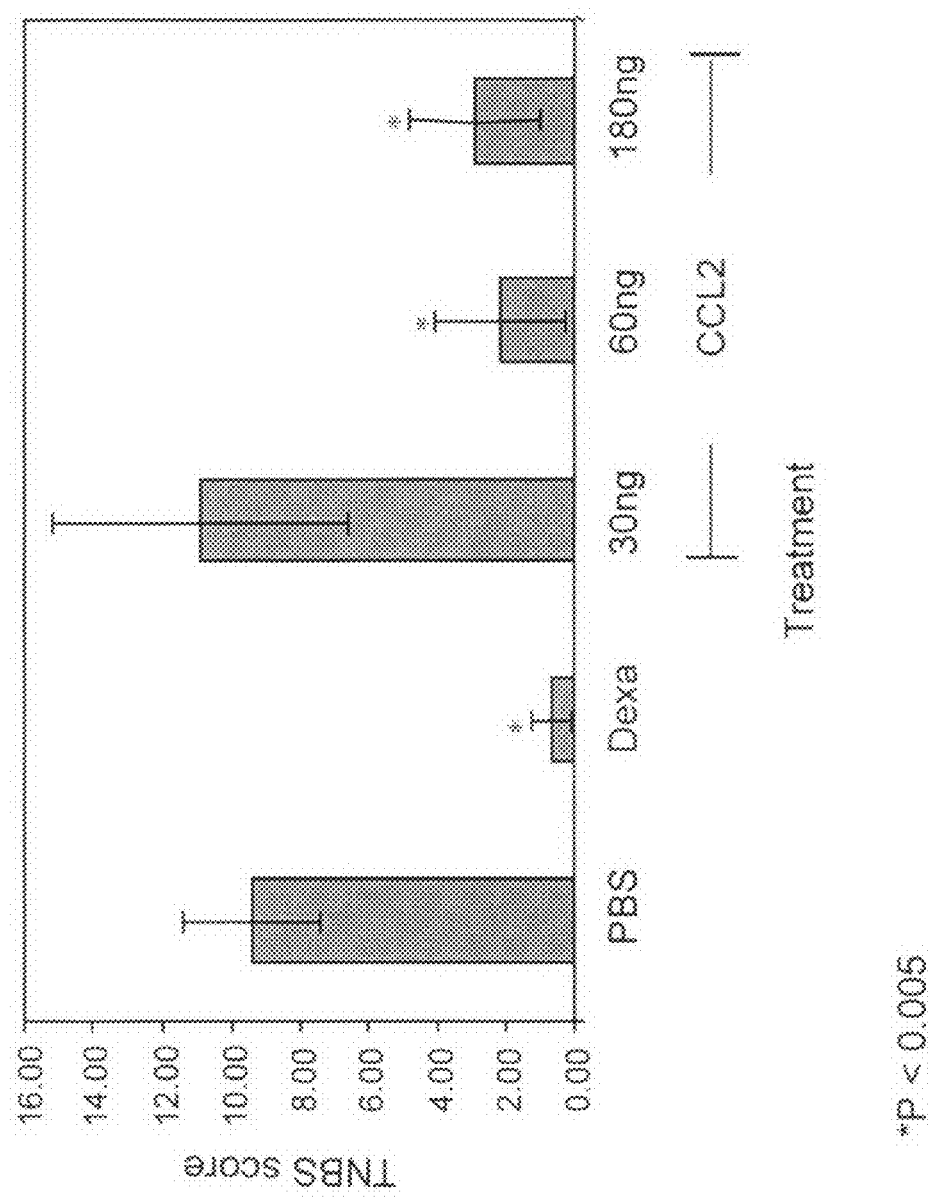
FIG. 10 is a graph depicting the inhibition of TNBS-colitis by CCL2 in a mouse model. TNBS-colitis was induced in mice as described in Example 6 and grouped according to dosing regime as follows: i.p. daily injection with different CCL2 concentrations (30 ng, 60 ng or 180 ng) from day 0 (immediately after TNBS induction) to day 6. Control groups were injected i.p. daily with PBS alone, with dexamethasone (Dexa) or remained untreated also negative control. The colon was evaluated microscopically for lesions according to the Wallace criteria (on a scale from 0 to 16 based on criteria reflecting inflammation, such as hyperemia, thickening of the bowel, and the extent of ulceration).

CCL2 plays an anti-inflammatory role in colitis—To examine the possible anti-inflammatory effect of CCL2 on inflammatory bowel disease (IBD), CCL2 was administered to mice following induction of TNBS colitis, the animal model for IBD. As clearly shown in Table 2 hereinbelow and in FIG. 10, CCL2 significantly inhibited the disease by reducing the severity of the inflammation as seen by the decrease in diarrhea and reduction in colon shortening.

TABLE 2

| Mice treatment | Mice number | Colitis score | Colon length (cm) | Diarrhea (# of mice) |
|---|---|---|---|---|
| Untreated | 1 | 0 | 9.5 | 0 |
| PBS | 5 | 9.4 ± 2 | 6.2 ± 0.27 | 3 |
| dexamethasone | 3 | 0.67 ± 0.58 | 8.17 ± 0.76 | 0 |
| 30 ng | 8 | 10.875 ± 4.29 | 6.25 ± 0.65 | 4 |
| 60 ng | 8 | 2.13 ± 1.89 | 7.88 ± 0.35 | 0 |
| 180 ng | 8 | 2.88 ± 1.89 | 7.88 ± 0.58 | 0 |

Taken together, the in vivo studies indicate that CCL2 displays significant anti-inflammatory activity in animal models for three of the major human inflammatory diseases, rheumatoid arthritis, inflammatory bowel disease and asthma.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications and GenBank Accession numbers mentioned in this specification are herein incorporated in their entirety by reference into the specification, to the same extent as if each individual publication, patent or patent application or GenBank Accession number was specifically and individually indicated to be incorporated herein by reference. In addition, citation or identification of any reference in this application shall not be construed as an admission that such reference is available as prior art to the present invention.

What is claimed is:

1. A method of treating an inflammation associated with a medical condition selected from the group consisting of allergy, rheumatoid arthritis, colitis and multiple sclerosis in a subject in need thereof, the method comprising administering to the subject chemokine (C-C motif) ligand 2 (CCL2) at a therapeutically effective amount of 0.1-0.6 µg/kg body weight, thereby treating the inflammation associated with a medical condition selected from the group consisting of allergy, rheumatoid arthritis, colitis and multiple sclerosis.

2. The method of claim 1, wherein the subject is a human subject.

3. The method of claim 1, wherein the inflammation is associated with CCR2/CCL2 dependent cell migration or homing.

4. The method of claim 3, wherein said cell migration or homing comprises T-cell migration or homing.

5. The method of claim 1, wherein said CCL2 comprises the amino acid sequence as set forth in GenBank Accession Number: NP_002973 (SEQ ID NO: 9).

* * * * *